US007517656B2

(12) United States Patent
Martin et al.

(10) Patent No.: US 7,517,656 B2
(45) Date of Patent: Apr. 14, 2009

(54) OPTICAL SENSOR AND METHODS FOR MEASURING MOLECULAR BINDING INTERACTIONS

(75) Inventors: Peter Martin, Kahului, HI (US); Keiki-Pua Dancil, Makawao, HI (US); Arthur Lee Morsell, Santa Rosa, CA (US); Hus Tigli, La Jolla, CA (US)

(73) Assignee: Trex Enterprises Corp., San Diego, CA (US)

( * ) Notice: Subject to any disclaimer, the term of this patent is extended or adjusted under 35 U.S.C. 154(b) by 592 days.

(21) Appl. No.: 10/616,251

(22) Filed: Jul. 8, 2003

(65) Prior Publication Data
US 2005/0019956 A1 Jan. 27, 2005

Related U.S. Application Data

(60) Provisional application No. 60/399,524, filed on Jul. 30, 2002.

(51) Int. Cl.
*C12M 1/34* (2006.01)
(52) U.S. Cl. .................. 435/7.1; 435/287.1; 435/287.2; 435/288.7; 435/808; 385/12; 385/129; 385/130; 422/82.05; 422/82.11
(58) Field of Classification Search .................. 356/301, 356/244; 428/446, 172; 257/13
See application file for complete search history.

(56) References Cited

U.S. PATENT DOCUMENTS 4,037,472 A * 7/1977 Gates ....................... 73/864.35
5,293,872 A * 3/1994 Alfano et al. ............... 600/475
6,248,539 B1 6/2001 Ghadiri
6,342,349 B1 * 1/2002 Virtanen ........................ 435/6
6,970,239 B2 * 11/2005 Chan et al. .................. 356/301
2002/0109134 A1 * 8/2002 Iwasaki et al. ................ 257/13
2002/0135772 A1 * 9/2002 Bornhop et al. ............. 356/450

OTHER PUBLICATIONS

Dudovich et al., Single-pulse coherent anti-stokes raman spectroscopy in the fingerprint spectral region, May 2003, J Chem Phys, 118(20) p. 9208-9215.*

* cited by examiner

*Primary Examiner*—Nelson Yang
(74) *Attorney, Agent, or Firm*—John R Ross

(57) ABSTRACT

Methods and devices for the measurement of molecular binding interactions. Preferred embodiments provide real-time measurements of kinetic binding and disassociation of molecules including binding and disassociation of protein molecules with other protein molecules and with other molecules. In preferred embodiments ligands are immobilized within pores of a porous silicon interaction region produced in a silicon substrate, after which analytes suspended in a fluid are flowed over the porous silicon region. Binding reactions occur when analyte molecules diffuse closely enough to the ligands to become bound. Preferably the binding and subsequent disassociation reactions are observed utilizing a white light source and thin film interference techniques with spectrometers arranged to detect changes in indices of refraction in the region where the binding and disassociation reactions occur. In preferred embodiments both ligands and analytes are delivered by computer controlled robotic fluid flow control techniques to the porous silicon interaction regions through microfluidic flow channels.

45 Claims, 19 Drawing Sheets

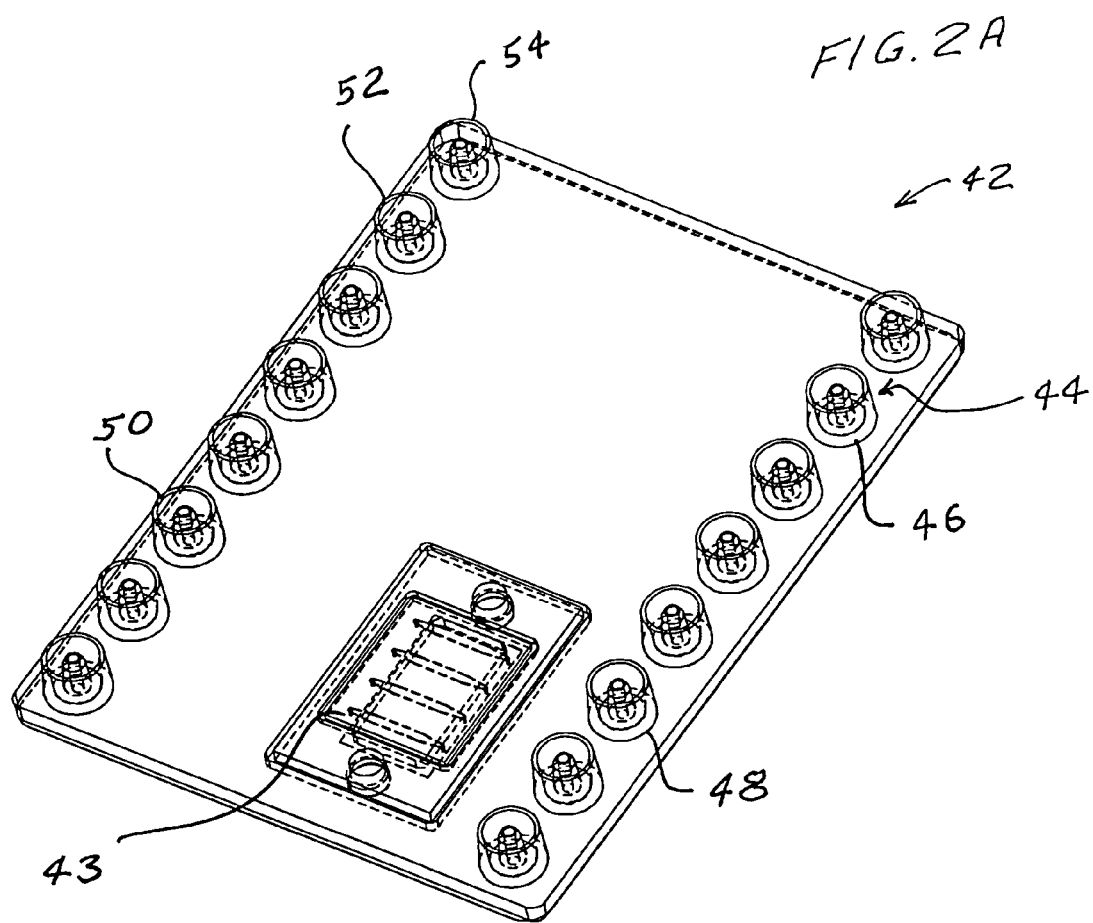

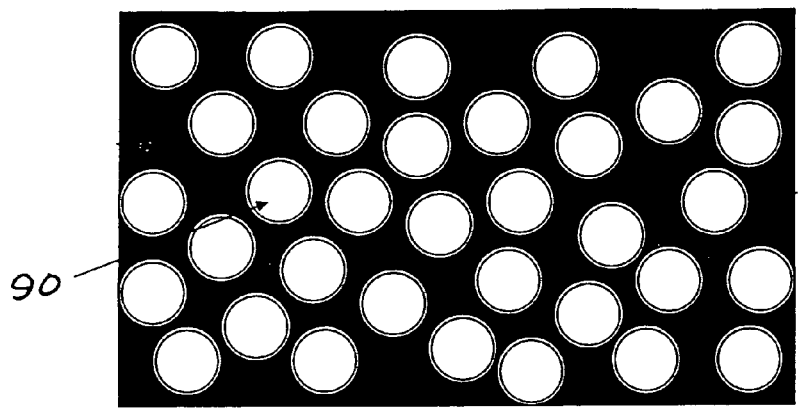
FIG. 7
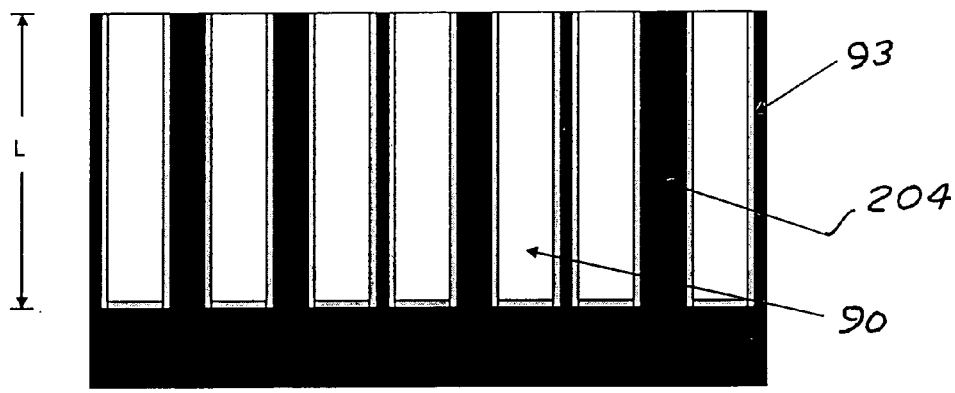
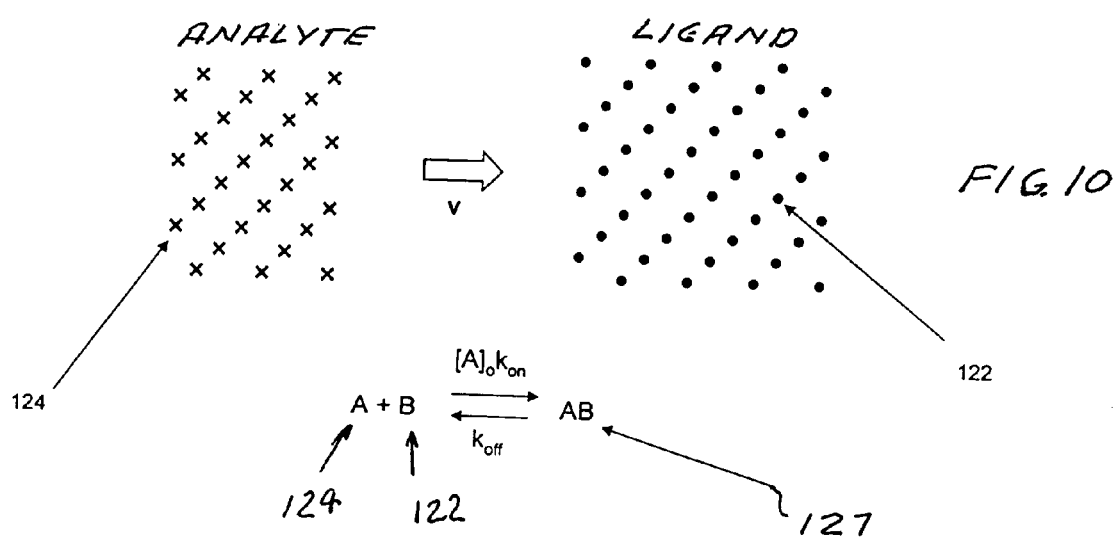
FIG. 10

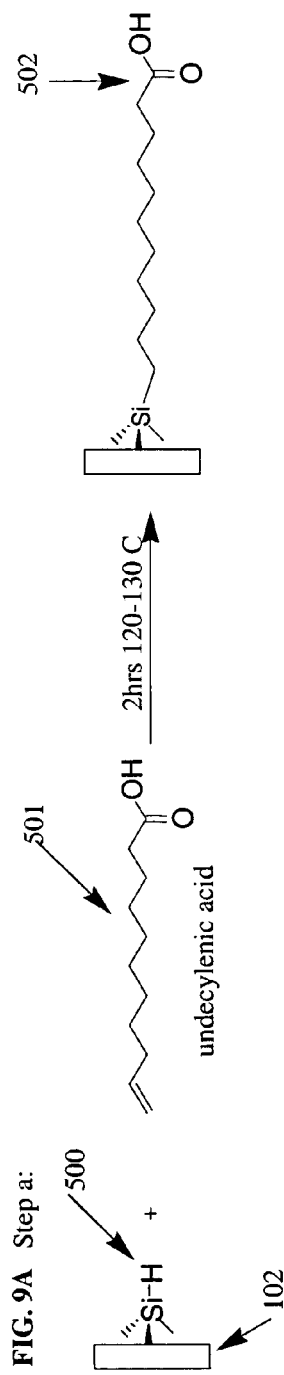
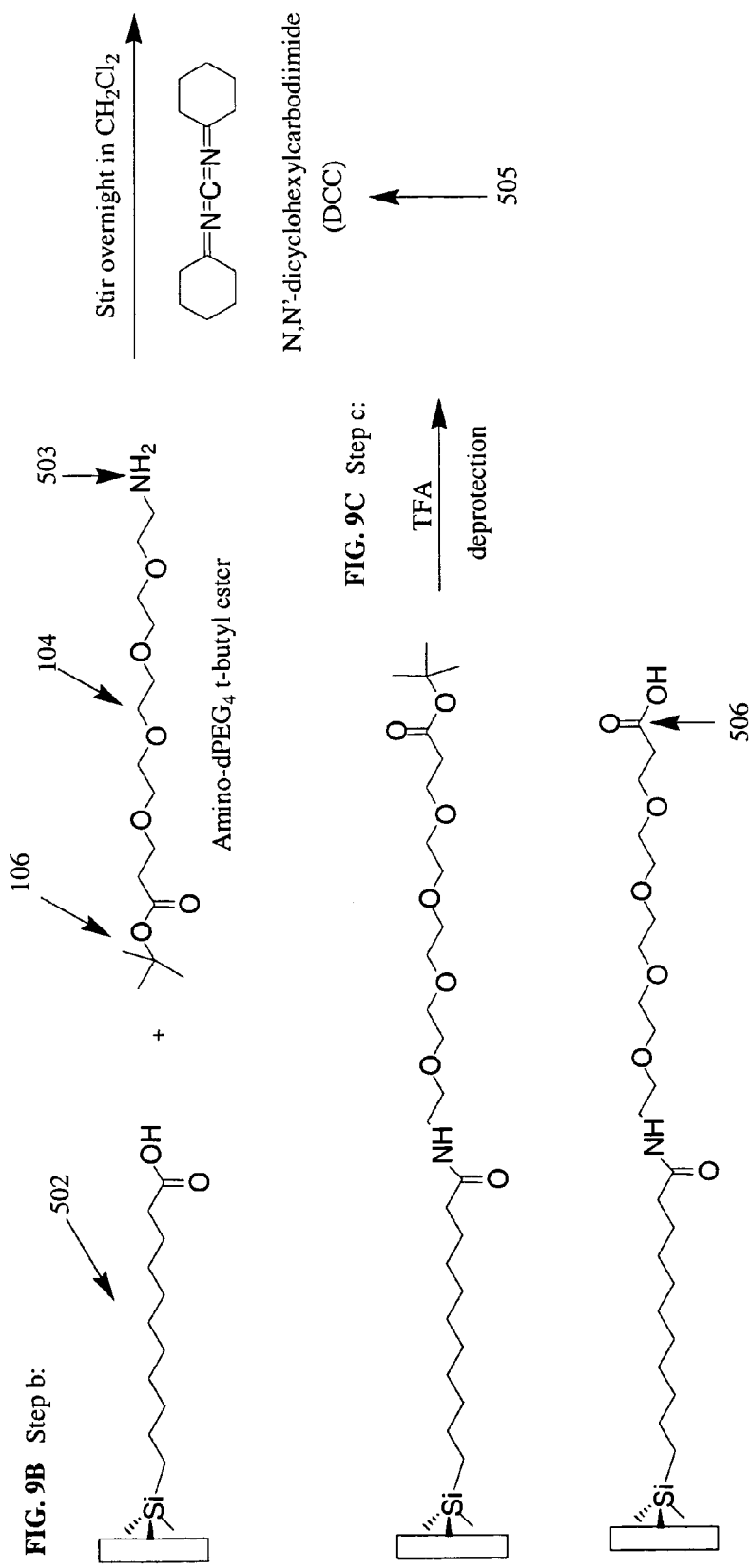

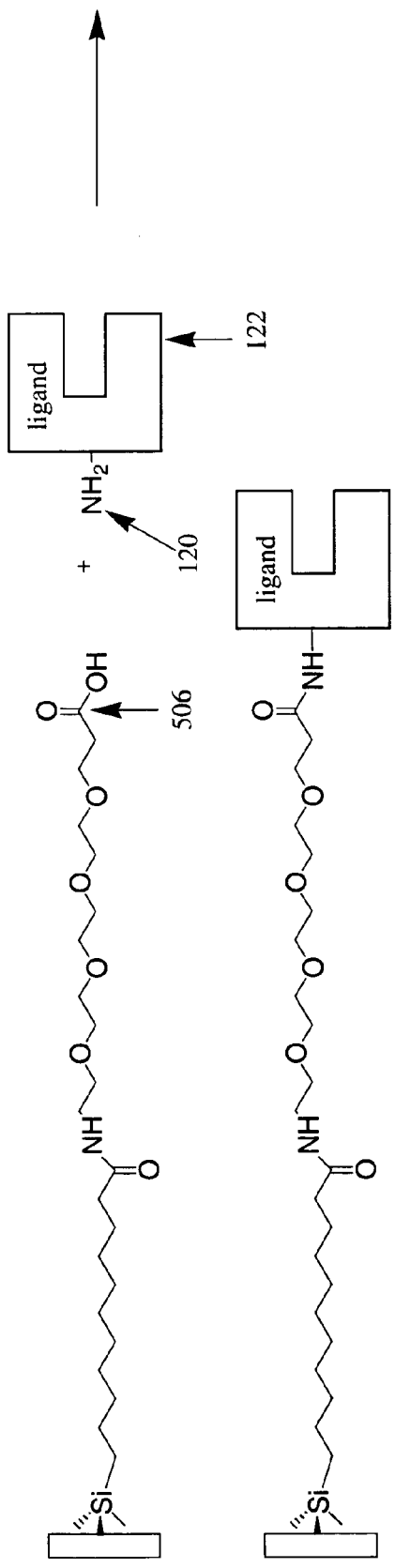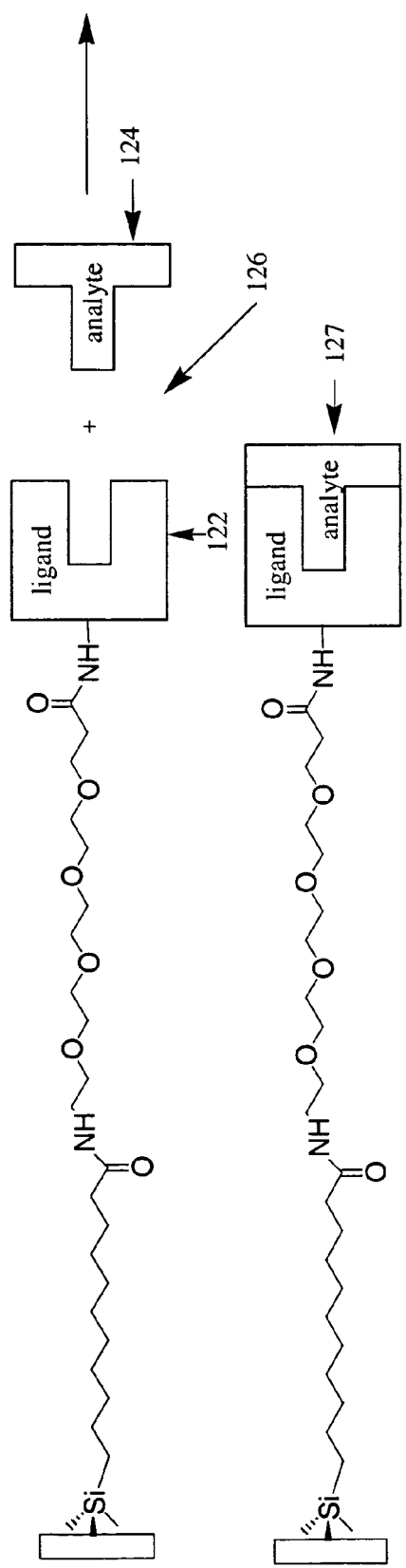
FIG. 9D Step d:
FIG. 9E Step e:

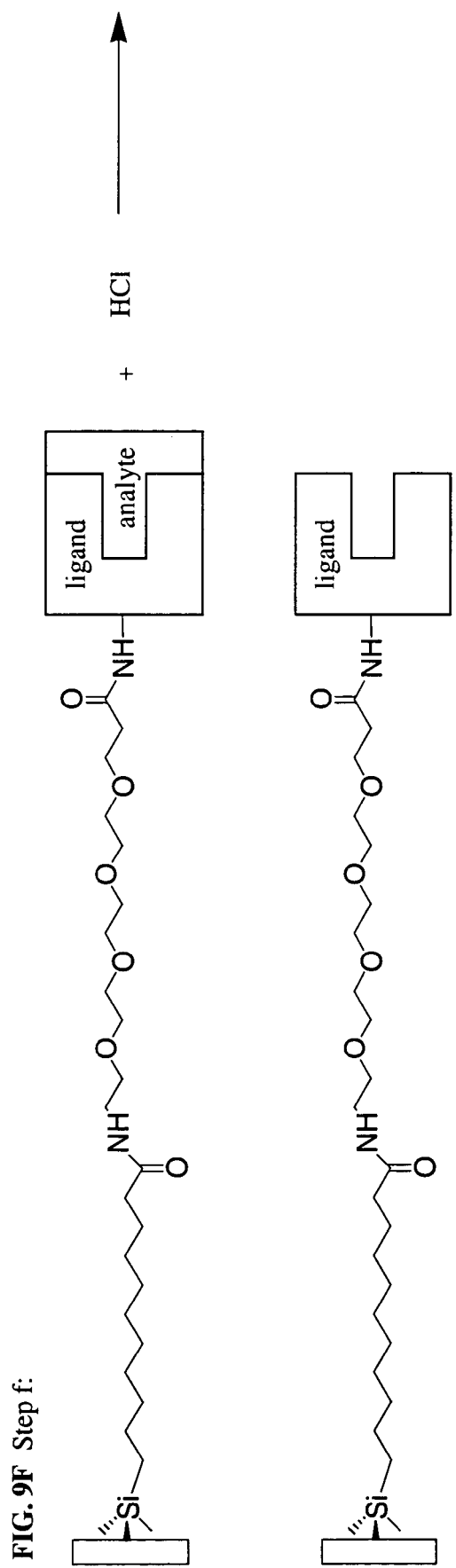
FIG. 9F Step f:

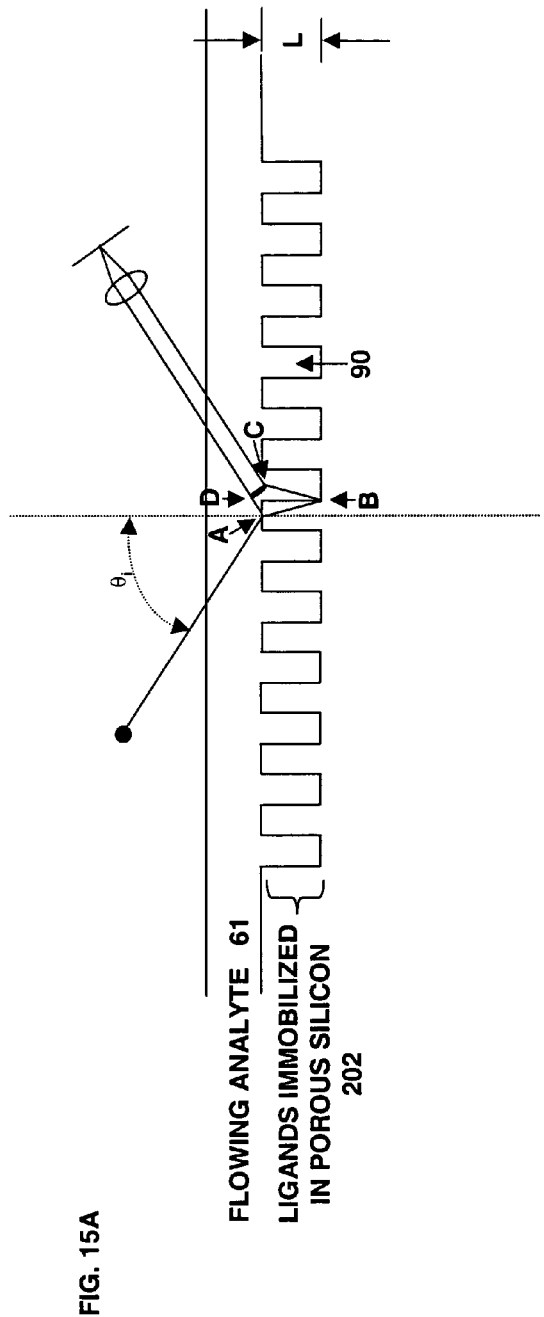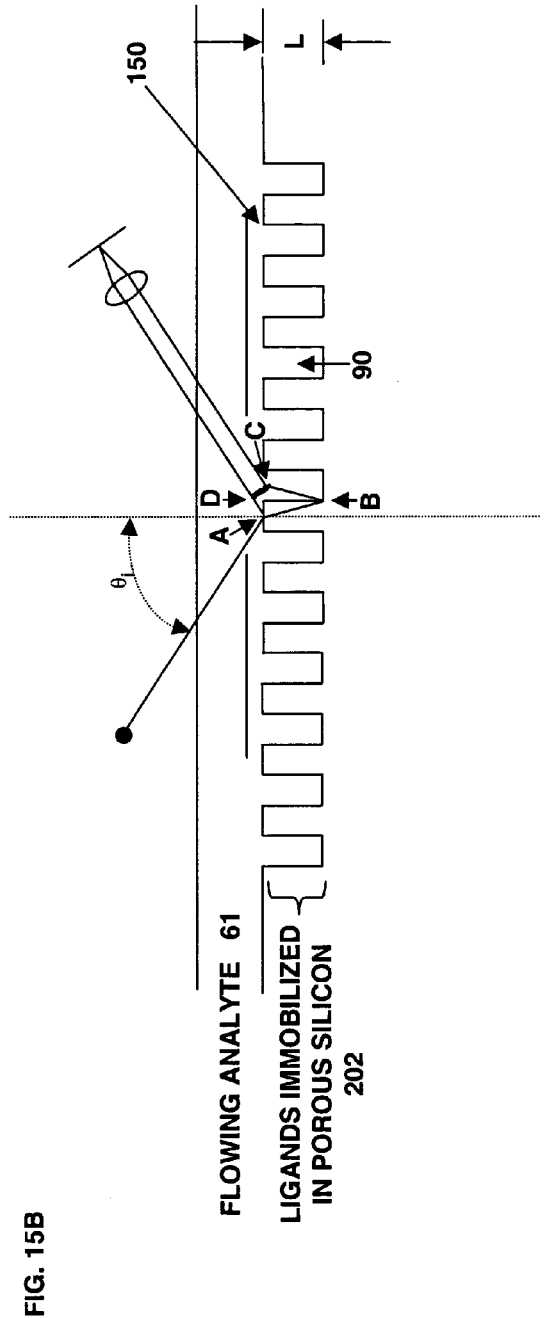

OPTICAL SENSOR AND METHODS FOR MEASURING MOLECULAR BINDING INTERACTIONS

This application claims the benefit of provisional patent application Ser. No. 60/399,524 filed Jul. 30, 2002. This invention relates to optical sensors and in particular to optical biosensors.

BACKGROUND OF THE INVENTION

The prior art includes a wide variety of optical sensors. An optical biosensor is an optical sensor that incorporates a biological sensing element. In recent years optical biosensors have become widely used for sensitive molecular binding measurements.

SURFACE PLASMON RESONANCE

An optical biosensor technique that has gained increasing importance over the last decade is the surface plasmon resonance (SPR) technique. This technique involves the measurement of light reflected into a narrow range of angles from a front side of a very thin metal film producing changes in an evanescent wave that penetrates the metal film. Ligands and analytes are located in the region of the evanescent wave on the backside of the metal film. Binding and disassociation actions between the ligands and analytes can be measured by monitoring the reflected light in real time. These SPR sensors are typically very expensive. As a result, the technique is impractical for many applications.

RESONANT MIRROR

Another optical biosensor is known as a resonant mirror system, also relies on changes in a penetrating evanescent wave. This system is similar to SPR and, like it, binding reactions between receptors and analytes in a region extremely close to the back side of a special mirror (referred to as a resonant mirror) can be analyzed by examining light reflected when a laser beam directed at the mirror is repeatedly swept through an arc of specific angles. Like SPR sensors, resonant mirror systems are expensive and impractical for many applications.

THIN FILMS

It is well known that monochromic light from a point source reflected from both surfaces of a film only a few wavelengths thick produces interference fringes and that white light reflected from a point source produces spectral patterns that depend on the direction of the incident light and the index of refraction of film material. (See "Optics" by Eugene Hecht and Alfred Zajac, pg. 295-309, Addison-Wesley, 1979.)

U.S. Pat. No. 6,248,539 (incorporated herein by reference) discloses an optical resonance technique that utilizes a very thin porous silicon layer within which binding reactions between ligands and analytes take place. The binding and disassociation affects the index of refraction within the thin porous silicon layer. Light reflected from the thin film produces interference patterns that can be monitored with a CCD detector array. The extent of binding can be determined from change in the spectral pattern.

KINETIC BINDING MEASUREMENTS

Kinetic binding measurements involve the measurement of rates of association (molecular binding) and disassociation. Analyte molecules are introduced to ligand molecules producing binding and disassociation interactions between the analyte molecules and the ligand molecules. Binding occurs at a characteristic rate $[A][B]k_{on}$ that depends on the strength of the binding interaction $k_{on}$ and the ligand topologies, as well as the concentrations $[A]$ and $[B]$ of the analyte molecules A and ligand molecules B, respectively. Binding events are usually followed by a disassociation event, occurring at a characteristic rate $k_{off}$ that also depends on the strength of the binding interaction. Measurements of rate constants $k_{on}$ and $k_{off}$ for specific molecular interactions are important for understanding detailed structures and functions of protein molecules. In addition to the optical biosensors discussed above, scientists perform kinetic binding measurements using other separations methods on solid surfaces combined with expensive detection methods (such as capillary liquid chromatography/mass spectrometry) or solution-phase assays. These methods suffer from disadvantages of cost, the need for expertise, imprecision and other factors.

SEPARATIONS-BASED MEASUREMENTS

More recently, optical biosensors have been used as an alternative to conventional separations-based instrumentation and other methods. Most separations-based techniques have typically included 1) liquid chromatography, flow-through techniques involving immobilization of capture molecules on packed beads that allow for the separation of target molecules from a solution and subsequent elution under different chemical or other conditions to enable detection; 2) electrophoresis, a separations technique in which molecules are detected based on their charge-to-mass ratio; and 3) immunoassays, separations based on the immune response of antigens to antibodies. These separations methods involve a variety of detection techniques, including ultraviolet absorbance, fluorescence and even mass spectrometry. The format also lends itself to measure of concentration and for non-quantitative on/off detection assays.

What is needed is a device and method for efficiently making molecular binding measurements, including kinetic molecular binding measurements as well as concentration and non-quantitative on/off detection assays.

SUMMARY OF THE INVENTION

This invention provides methods and devices for the measurement of molecular binding interactions. Preferred embodiments provide real-time measurements of kinetic binding and disassociation of molecules including binding and disassociation of protein molecules with other protein molecules and with other molecules. In preferred embodiments ligands are immobilized within pores of a porous silicon interaction region produced within a crystalline silicon substrate and analytes are diluted in a fluid (buffer) and flowed over the porous silicon region. Binding reactions occur after analyte molecules diffuse closely enough to the ligands to become bound. Preferably the binding and subsequent disassociation reactions are observed utilizing a white light source and thin film interference techniques with spectrometers arranged to detect changes in indices of refraction in the region where the binding and disassociation reactions occur. In preferred embodiments both ligands and analytes are delivered by computer controlled robotic fluid flow control techniques to the porous silicon interaction regions through microfluidic flow channels. In a prototype unit designed as tested by applicants, four interaction regions are provided each with its own fluid delivery system and spectrometer so that up to four binding measurements can be made simultaneously. A special kinetic binding measurement model is provided to calculate apparent changes in the optical path difference (OPD) of each of the interaction regions from spectral patterns produced by spectrometers. In preferred embodiments these apparent changes in OPD are used to determine binding and disassociation rates.

In preferred embodiments novel techniques are used to immobilize the ligands in the porous silicon regions. Linker molecules are utilized to link the ligands to specially treated surfaces within the pores of the porous silicon. Preferred linker molecules includes a polyethylene glycol molecule specially assembled to link to the specially treated walls of the pores. These linker molecules in turn link to a variety of biomolecules, which function as ligands in the binding reactions with analytes of interest. Preferred embodiments of the present invention are capable of measuring surface concentrations of proteins at precision levels of 1 picogram per square millimeter.

BRIEF DESCRIPTION OF THE DRAWINGS

FIG. 2A. is a prospective drawing of the FIG. 2 cartridge.

FIGS. 6A-C drawings are showing optical features of a preferred embodiment.

FIG. 7 is drawing showing magnified features of a porous silicon interaction region.

FIGS. 9A-9F is a drawing showing techniques for linking a ligand to the walls of the pores in a porous silicon region.

FIG. 10 demonstrates binding and disassociation between a ligand and an analyte.

FIGS. 15A and 15B demonstrates a technique for measuring binding reactions where optical path changes occur just above a porous silicon region.

DETAILED DESCRIPTION OF PREFERRED EMBODIMENTS

Observing Small Things with Long Wavelength Light

For an understanding of the present invention the reader should keep in mind the sizes of various elements involved in the present invention. It is important to understand that, with this device, applicants are monitoring real time interactions of molecules such as proteins having dimensions as small as a few nanometers with visible light having wavelengths in the range of about 400 nm to 700 nm. These molecules are much too small to be imaged with light in these wavelengths; however, actions of these molecules can be determined because the speed of light is affected by their presence or absence in an interaction region. A light beam reflects from a top surface and a bottom surface of a thin porous silicon region to produce two reflected beams that interfere with each other. The interference produces spectral patterns that are a function of a phase delay of one of the beams relative to the other. This delay represents an apparent optical path difference and is referred to as an OPD. This OPD between the reference beam and the beam passing through the molecule containing solution can be monitored. Changes in the concentration of molecules within the interaction region produce apparent changes in the OPD. These apparent changes in OPD thus provide a measure of the concentration of the molecules in the solution.

The Optical Biosensor

Figure 1:
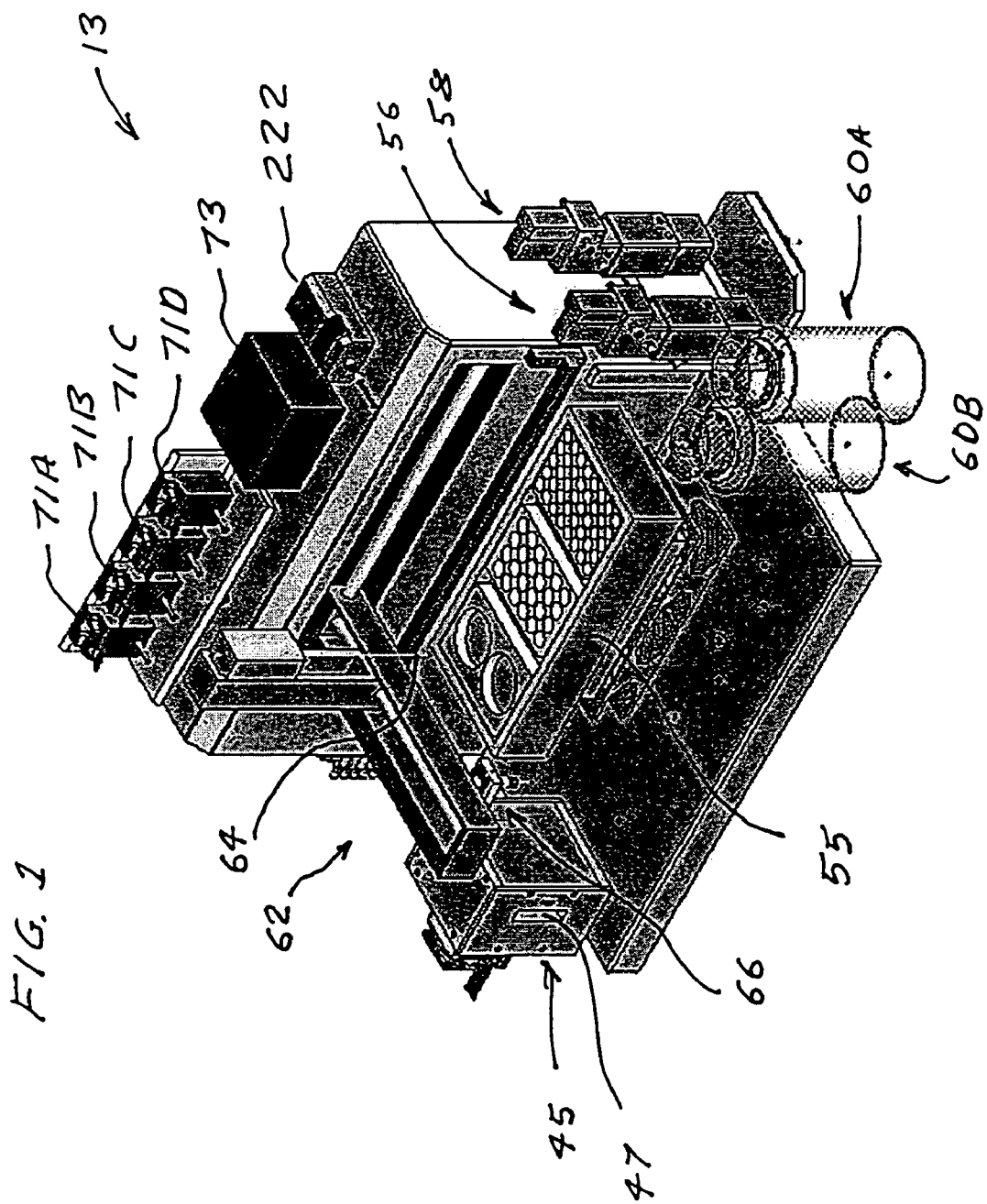
FIG. 1 is a drawing of a preferred optical biosensor unit according to the present invention.
Figure 2:
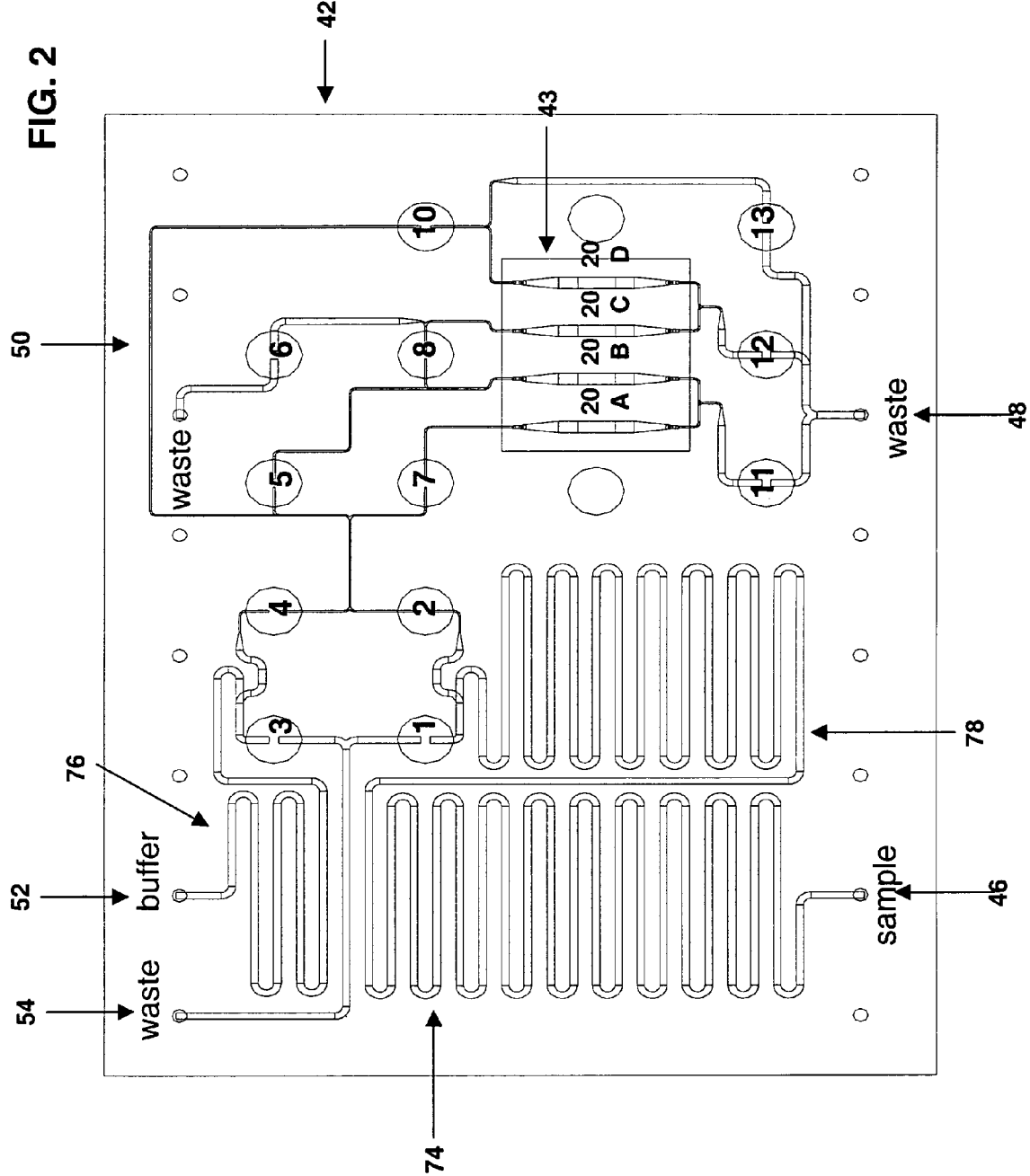
FIG. 2 is a drawing showing flow channels and observation regions of a disposable fluidics cartridge.

FIG. 1 is a prospective drawing showing some of the features of an optical biosensor 13 which uses a four channel fluidics cartridge for monitoring binding reactions. This unit includes robotic equipment 62, four spectrometers 71A, B, C and D, light source 222, sample trays 55, buffer fluid tank 60A and waste tank 60B, sample pump 56 and buffer pump 58, sample injection port 66, control box 73 and pneumatic controls, firmware and software necessary for automated real-time measurements. In this unit a small (1.7 inch×2.3 inch) disposable cartridge 42 shown in FIGS. 2 and 2A provides four interaction regions at which molecular binding interactions can be optically observed. The disposable cartridge is inserted into fluidics enclosure 45 at location 47. Light from point light sources reflects from the top and bottom surfaces of each of each of the interaction regions and produces spectral interference patterns which are monitored in order to gather information regarding molecular binding interactions.

Fabrication of Porous Silicon

In preferred embodiments these binding interactions occur in porous silicon regions of cartridge 42. The porous silicon regions are high surface area regions consisting of nanometer size pores in a crystalline silicon substrate. The pores are produced by an anodic electrochemical etch of bulk crystalline silicon. The starting material for porous silicon, for preferred embodiment, is a heavily doped crystalline silicon wafer, commercially available for semiconductor manufacturing purposes. Typical wafer specifications for porous silicon fabrication include $p^{++}$-type boron doped silicon (0.6-1.0 mΩ-cm resistivity), <100>crystal orientation. The wafer is immersed in an ethanolic hydrofluoric acid solution (HF: ethanol, 3(v):1(v)) and a constant electric current is applied to the silicon wafer using a platinum electrode. The silicon atoms at the silicon/electrolyte interface are polarized, and are subject to attack by the fluoride ions in solution. Silicon atoms are released in the form of silicon hexafluoride. Porous silicon tends to etch as a distribution of long cylindrical nanotubes or pores 90 as shown in FIG. 7. The distribution of pore diameters and the depth of the pores are controlled by adjusting the current density and the etching time. Typical pore features for this invention are pore diameter distributions of 80 to 120 nanometers and pore depths of 1000 to 3000 nanometers. The depth of the pores is very uniform. This high uniformity of the etching process provides the two optically flat interfaces; the top surface 208 of the porous silicon, and the interface 210 between the bottom of the porous silicon region and the non-porous, or bulk, silicon. Additional details relating to this process are contained in U.S. Pat. No. 6,248,539 that has been incorporated herein by reference.

For use in the present invention forty four porous silicon regions having dimensions of 2 mm×11 mm are etched into a 100 mm silicon wafer. The wafer is then diced up into forty four individual die having dimensions of 10 mm×13 mm. Each referred to a porous silicon die part 43. Flow channels about 2 mm wide are produced across the top of the porous silicon regions 202 with a machined plastic window 207 which is attached with epoxy to the silicon die 43. A transparent plastic window 207 forms the top of the flow channels. Four flow channels 20A, 20B, 20C and 20D are thus created on each die part 43 and is incorporated into a plastic fluidics cartridge 42 containing elaborate microfluidic channels and pinch valves, all as shown in FIG. 2 and FIG. 2A. Molecular interactions that occur in the porous silicon regions 202 at the bottom of the flow channels are observable through the transparent plastic window 207. We will refer in this specification to these regions of molecular interaction as interaction regions in some places and as observation regions in some cases.

Figure 3:
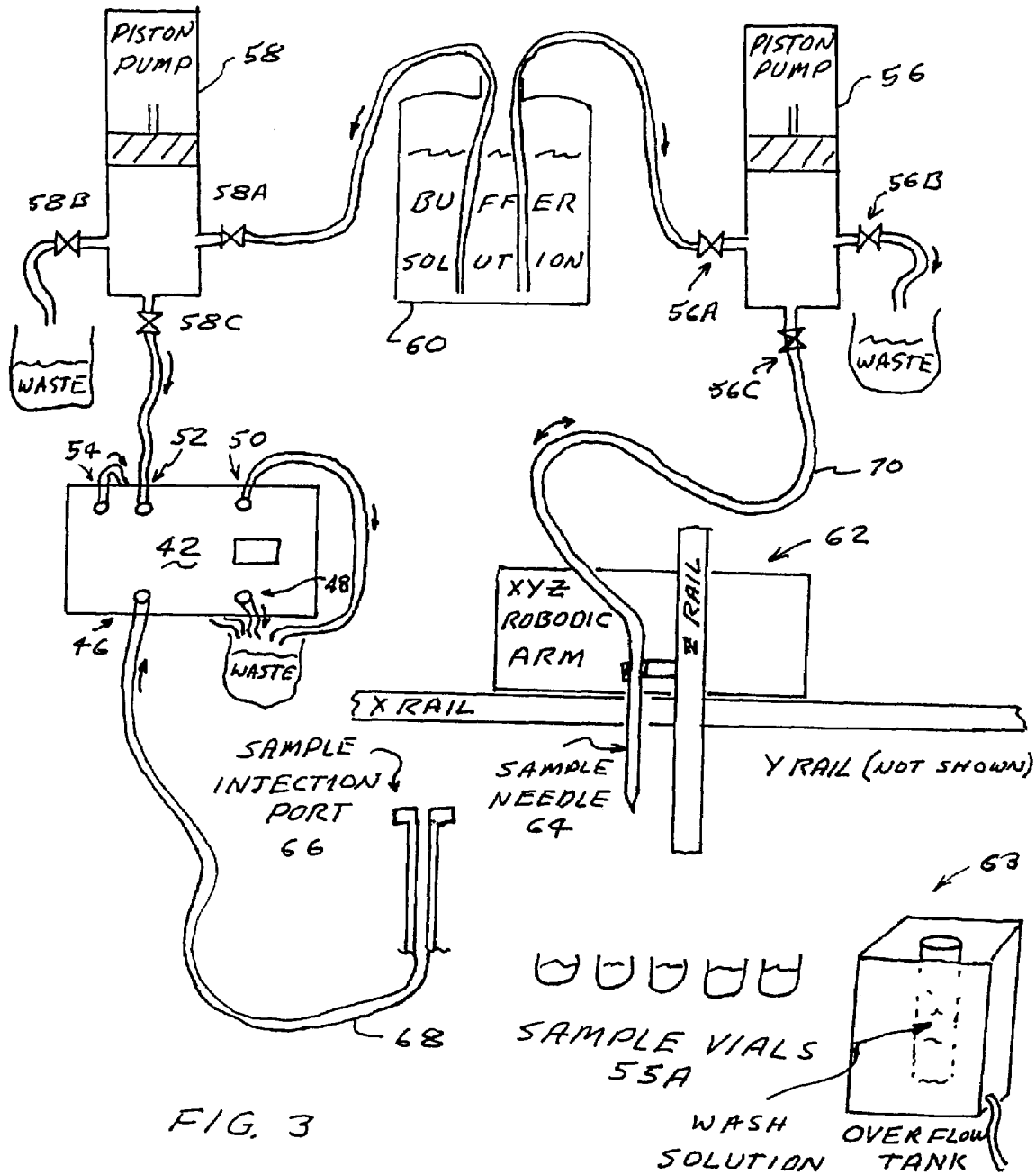
FIG. 3 is a cartoon drawing showing some of the features a preferred features of the present invention.

FIG. 2 shows the four observation regions 20A, B, C, and D and flow channels for delivering sample fluids and buffer fluids to the four observation regions and for exhausting waste fluids. The fluidics cartridge includes 12 pneumatically controlled pinch valves 1-12. FIG. 2A is a prospective view of cartridge 42. The cartridge comprises the female portions of small tubing couplings 44. In this particular cartridge only five of the couplings are utilized as shown at 46, 48, 50, 52, and 54; the rest are blanks. In this embodiment, couplings 46-54 are automatically connected to mating sample, waste and buffer fluid channels in parts of the biosensor unit when the cartridge is inserted into its operating position in enclosure 45. These fluid channels include three waste channels connected to female coupling parts 54, 50 and 48, a sample channel in flow communication with coupling part 46 and a buffer flow channel in flow communication with coupling part 52. As shown in FIG. 3 the unit includes a one-half liter buffer tank 60 containing buffer solution and a first fluid pump 58, called the buffer pump, with valves 58A, 58B and 58C providing controlled buffer fluid flow at any flow rate between 1 to 100 microliters per minute. A preferred pump is a positive displacement piston pump available from Sapphire Engineering a division of Scivex Inc., with offices in Waltham, Mass. Buffer flow from this pump enters the cartridge at location 52. The unit also includes a second fluid pump 56, called the sample pump, which like pump 58 is a positive displacement pump for providing both sample and buffer fluid flow into the fluidics cartridge at sample port 46. This pump 56 comprises valves 56A, 56B and 56C.

Fluid Flow

FIGS. 2, 3, 4 and 5 can be referred to in order to understand some of the typical automated steps for introducing both ligand and analyte into the observation regions (for example observation region 20A shown in FIG. 2). As explained above observation regions 20A, B, C and D include flow channels with the porous silicon regions forming the bottom of the flow channels. The observation regions each provides an optically observable region for immobilizing particular ligands which in turn bind to particular analytes which diffuse into and out of the porous silicon regions from a buffer solution flowing over the porous silicon regions. The objective of many experiments is to monitor this binding action and also in many cases a subsequent disassociation of the analyte from the ligand.

Portions of cartridge 42 may be flushed using buffer pump 58. Buffer solution can be pulled by pump 58 from tank 60 by closing valves 58B and C and opening valve 58A. The solution can then be pumped into cartridge 42 through port 52 to flush regions of the cartridge. Regions to be flushed are chosen by opening or closing various combinations of pinch valves 1-12 as shown in FIG. 2. Other portions of the cartridge can be flushed using sample pump 56. To do this, as shown in FIG. 3, computer controls are used to position robotic arm 62 so that sample needle 64 is inserted firmly into injection port 66 which is connected by tubing 68 to cartridge sample port 46. Similarly as above, pump 56 can pump buffer solution through flexible tubing 70, needle 64 and tubing 68 into sample port 46. As above, regions to be flushed are selected by appropriate combination of open and closed pinch valves 1-12 of cartridge 42. A preferred automated robotic liquid handling system is Gilson Model 223 available from Gibson, Inc. with offices in Middleton, Wis.

Ligands and analytes may be flowed through observation regions 20A, B, C and D using sample pump 56 with computer controlled robotic arm 62. Ligands and analytes are located in sample vials in preselected locations as shown at 55 in FIG. 1. A few of these vials are also shown in FIG. 3 at 55A. A sample such as a ligand or an analyte is drawn from one of the vials 55A into needle 64 by closing valve 56C and 56B and opening valve 56C. Needle 64 is then moved by robotic arm 62 to port 66 and the sample is injected into cartridge 42 through port 46. Preferably, needle 64 is loaded with air bubbles on both sides of a useful slug of sample as shown at 72 in FIG. 5. This prevents diffusion in the needle and flow channels of sample and buffer. A portion of the sample along with the air bubbles and some buffer is disposed as waste by appropriate valve control using valves 1-12 in cartridge 42.

Kinetic Molecular Binding Measurements

In preferred applications of the present invention protein molecules diluted in a buffer fluid are delivered to observation region 20A, B, C and D in order to set the initial conditions for kinetic binding measurements. The protein molecules bind to the pore walls at selected surface concentrations (pg/mm$^2$) via special linker molecules. These protein molecules then function as ligands in a binding interaction to be monitored. Then, analyte molecules are delivered to the region in time sequences in order to provide real-time, kinetic binding measurements. Disposable microfluidics cartridge 42, displayed in FIG. 2, is a key component of fluid delivery subsystem. As described above, cartridge 42 contains microfluidic channels 74, approximately 25-75 microns wide, and pinch valves 1-12 to provide flow control. Silicon die 43, containing four observation regions 20A, B, C and D is incorporated in cartridge 42. An optical window 207 covers four observation regions and forms the top of four flow channels through the observation region. There is space of about 50 microns between the top of the porous silicon and the bottom of the window. Valves 1-12 along with pumps 56 and 58 are utilized as described above and are computer controlled to provide buffer solution, ligands, and analyte flow through the observation regions 20A, B, C, and D in order to perform desired binding analysis. Temperature equilibration regions 76 and 78 provide heat transfer for each upstream flow path in order that buffer, ligand and analyte fluid samples are delivered at a precisely controlled temperature.

FIGS. 6A and 6B show the integration of the optical and fluid delivery systems. The disposable fluidics cartridge 42 is thermally mounted on thermal block 82 in order to provide thermal control of both thermal equilibration regions 76 and 78 and the observation regions 20A, B, C, and D. A Peltier thermoelectric device 84 and a thermocouple temperature monitor 86 provide active temperature control of thermal block 82. Each of the four observation regions incorporates a separate optical measurement subsystem, as shown in FIGS. 6A and 6B. Four point white light sources are produced by white light lamp 222. Light from the lamp is collected into a single optical fiber and this fiber feeds the light into four separate optical fibers 236, A, B, C, and D shown in FIGS. 6A and B. Light reflected from the four observation regions is collected in optical fibers 240A, B, C and D as shown in FIGS. 6A and 6B and delivered by the fibers to spectrometers 71A, B, C and D as shown in FIG. 1. As shown in FIG. 6C for each of the four optical systems (A B C and D), a lens 241 collimated the light from input fiber 236 and directs it at a slight angle to its respective observation region. Reflected light from the region is focused by the same lens into output fiber 240 which carries the reflected light to the respective spectrometer 71 (A B C or D).

Figure 8:
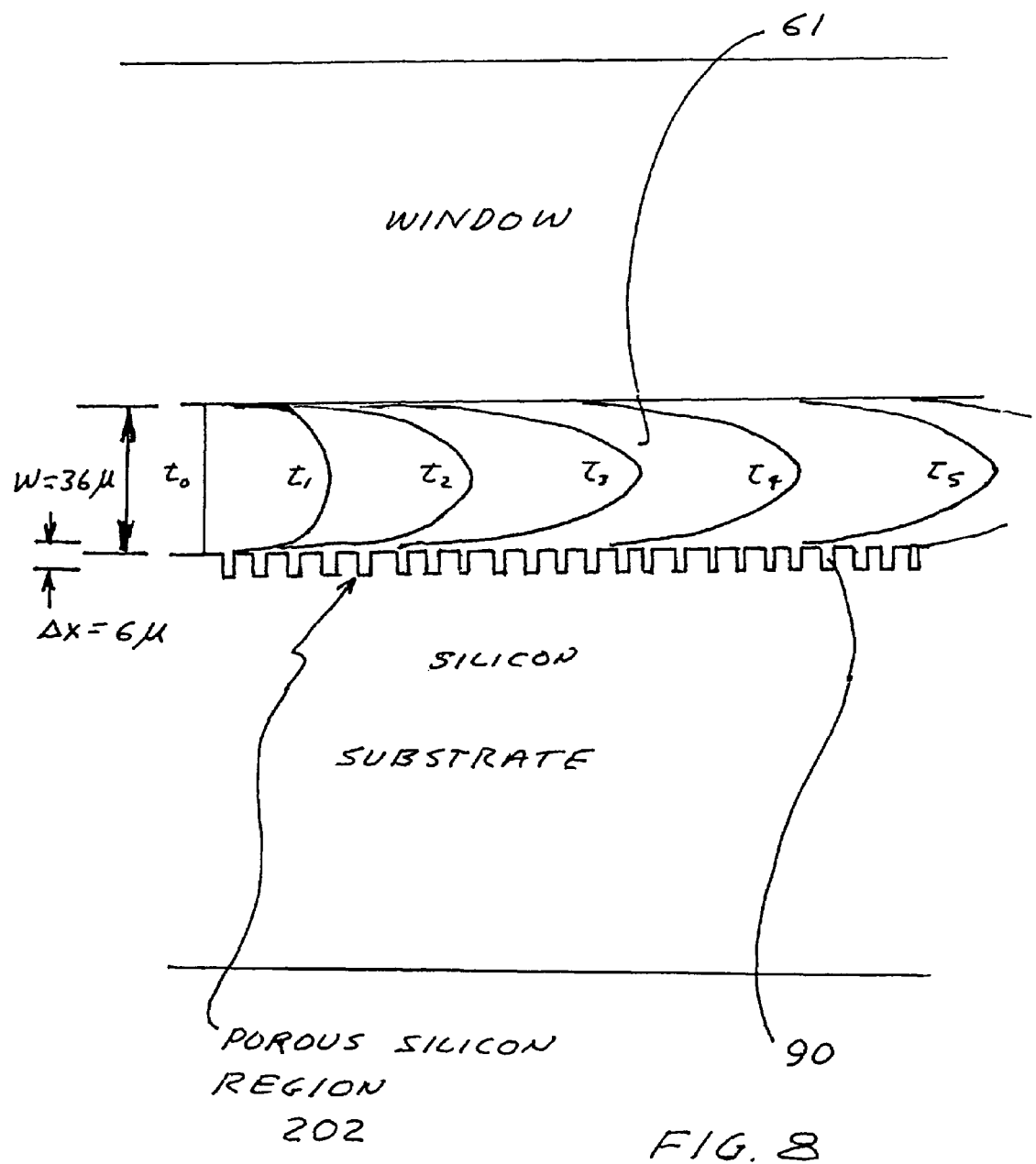
FIG. 8 is a drawing showing sample flow over a porous silicon interaction region.

For measurement of kinetic binding reactions, the concentration of analyte molecules $[A]_0$ in the observation regions (such as observation region 20A) should preferably remain as constant as feasible throughout the observation region during the measurement. This experimental condition is preferably achieved by (1) providing a continuous flow rate of analyte molecules through flow channel 61 directly above porous silicon region 202 or 150 and (2) allowing the basic diffusion mechanism to transport the analyte molecules into and out of the pores 90. FIG. 8 shows the basic geometry of the fluid flow in flow channel 61 above the porous silicon. The ideal flow sequence involved in a kinetic binding measurement features a blunt fluid interface, at time $t=t_0$, between the buffer and analyte/buffer solutions directly upstream of observation region 20A. The analyte/buffer solution is located to the left of the $t=t_0$ interface profile as shown in FIG. 8 and the buffer solution is located to the right of the $t=t_0$ interface profile. Before $t=t_0$, the buffer solution fills the pores 90 of observation region 20A, thus setting the baseline optical path differences of region 20A. At time $t=t_0$, the flow system starts the flow of analyte/buffer solution via operation of the piston pump 56. FIG. 8 shows the parabolic fluid interface profiles between analyte/buffer and buffer solutions for successive times $t=t_1$ through $t=t_5$ that are a direct result of the parabolic-shaped fluid velocity profiles and the boundary condition that the velocity profiles terminate at zero velocity at the top and bottom walls of flow channel 61. Fluid flow prevents any significant quantity of the analyte/buffer solution to directly reach the surface of porous silicon observation region 20A, however, the parabolic fluid interface becomes infinitesimally closer to the surface of the region as time progresses. The basic diffusion mechanism enables the transport of analyte and buffer molecules across the fluid flow lines and into the porous silicon observation region. For some rough simplified calculations, to estimate the time for analytes to diffuse down into the pores 90, we will refer to this distance between the bottom of the flow region and the mid region of the porous silicon interaction region 111 as a distance $\Delta x$. The average time T that diffusion will transport an analyte molecule a distance $\Delta x$ is roughly estimated by:

$$\tau = (\Delta x)^2 / D \qquad \text{Eq. (47)}$$

where D [in units of $(cm)^2/sec$] is the diffusion constant for a particular molecule. Diffusion constants for large biomolecules are typically in the D=2 to $5 \times 10^{-7}$ cm$^2$/sec range. The design of flow channel 61 as shown in FIG. 8 provides a flow channel with a top to bottom width w of about 36 µm and the average flow velocities in the range of 1 to 5 cm/sec. The analyte/buffer solution should be introduced, into the flow channel 61 quite close (such as 3-5 mm) to the porous silicon observation region. For example, an analyte molecule flowed to a location that is 6 µm on the average from ligand molecules immobilized within pores in the porous region of porous silicon die part 43, will diffuse to the ligands in a time $\tau$ of about $(6 \mu m)^2/(5 \times 10^{-7}$ cm$^2$/sec$)=0.7$ sec. The average kinetic binding time constants are approximately 30-90 seconds or larger, so the diffusion time roughly calculated according to equation (47) will have negligible effect on the measurement of these binding constants.

Example Demonstrating Chemical Features of Preferred Embodiments

In addition to providing the key component for the optical measurement subsystem, the porous section observation regions 20A, B, C and D also serve as three-dimensional scaffolds to immobilize specific molecules. The regions provide a very large surface area in the form of cylindrical walls of pores 90. Ligand molecules are attached, or bound, to the pore walls 90 by the use of specific linker molecules. The linker molecules are attached to the pore walls by the use of surface chemistry, and the ligand molecules are then attached to the linker molecules.

FIGS. 9A-9F show a specific set of molecular interactions involved in an example of an application of the present invention. FIGS. 9A and 9B show steps a) and b) of a preferred method for immobilizing ligand protein molecules to the walls of pores 90. Steps a) and b) preferably are performed in a laboratory independent of the device shown in FIG. 1 and steps 9C-9F take place within the FIG. 1 device. The immobilization procedure is given here:

a) Hydrosilation of Porous Silicon Surface

The walls 102 of pores 90 of freshly etched porous silicon consists of hydride (Si—H) terminated silicon atoms as shown at 500 in FIG. 9A. The first step (step a) involves the hydrosilation of the hydride terminated porous silicon surface to produce a carboxylic acid functionalized (RCOOH) surface as shown at 502 in FIG. 9A. The preferred hydrosilation method involves exposing the hydride-terminated surface 500 to undecylenic acid 501 for two hours at an elevated temperature of 120 to 130 degrees Celsius.

b) Link Amino-dPEG$_4$ t-butyl ester to carboxylated Terminated Porous Silicon Surface Amino-dPEG$_4$ t-butyl ester (NH$_2$-dPEG$_4$-t-butyl ester) is a commercially available linker molecule (Quanta Biodesign Ltd. with offices in Powell, Ohio) that consists of a polyethylene glycol molecule 104 (called PEG) with an amine (NH$_2$) group 503 attached to one end and a tert-butyloxycarbonyl (t-boc) group 106 attached to the other end of the PEG molecule 104, all as shown in FIG. 9B. The PEG molecule 104 consists of a plurality of PEG monomers, defined as $(-CH_2-CH_2-O-)_x$. The preferred length of the PEG molecule 104 is four PEG monomers; equivalent to a total length of about 19.2 angstroms (1.92 nm). The t-boc group 106 acts as a non-reactive cap that serves as a protecting group for the carboxylic acid on the molecule. It is not removed until an acid deprotection step that occurs within cartridge 42 after it is mounted in the FIG. 1 device. The NH$_2$-dPEG$_4$-t-butyl ester compound is dissolved in methylene chloride and the carboxylated terminated porous silicon die 43 is placed in a flask containing the $NH_2$-$dPEG_4$-t-butyl ester-methylene chloride solution. N,N'-dicyclohexylcarbodiimide (DCC) shown at 505 is added to the $NH_2$-$dPEG_4$-t-butyl ester-methylene chloride solution. DCC is used to facilitate the amide bond formation between the carboxylic acid terminated porous silicon surface 504 and the $NH_2$-$dePEG_4$-t-butyl ester compound. For twelve hours under an inert atmosphere, such as nitrogen, the reaction enables the amine terminated end 503 of the $NH_2$-$dePEG_4$-t-butyl ester compound to attach to the carboxylic acid terminated walls pores. The preferred method involves the linking of $NH_2$-$dePEG_4$-t-butyl ester molecules to the entire surface area of the pores 90 in the porous silicon observation regions 202. After this step, the porous silicon die 43 is incorporated in the microfluidics cartridge 42 as shown in FIGS. 2 and 2A and cartridge 42 is installed in the FIG. 1 optical biosensor device.

c) Create Reactive Carboxylic Acid Terminated Surface in Microfluidic Cartridge

The microfluidics cartridge 42 now containing the $NH_2$-$dPEG_4$-t-butyl ester prepared silicon die 43 is placed in FIG. 1 device for the remaining steps. Trifluoroacetic acid is flowed through a flow channel 61 (such as 20A). The acid diffuses into the pores 90; this removes the t-boc group 106, leaving a reactive carboxylic acid group (COOH) as shown at 506 in FIG. 9C. A solution of 1-(3-dimethylaminopropyl-3-ethylcarbodiimide) (EDC) molecules 110 and sulfo-N-hydroxysuccinimide (sulfo-NHS) ester molecules 112 is then flowed through flow channel 61 (as shown in FIG. 8). The advantage of adding sulfo-NHS to EDC reactions is that they are highly efficient and create stable intermediates which will eventually react with the amine of interest. EDC reacts with the carboxylate group on the deprotected $NH_2$-$dPEG_4$-t-butyl ester, creating an active O-acylisourea leaving group. Forming a sulfo-NHS ester intermediate by reacting the hydroxyl group on the sulfo-NHS with the O-acylisourea extends the half life of the activated carboxylate to hours from seconds. The resulting surface is a NHS reactive binding site available for protein type conjugation via primary amines.

d) Immobilize Ligand Molecules to NHS Surface

In this preferred embodiment, the NHS modified surface will attach to free amine (R—$NH_2$) groups 120 located on the amino acid lysine which is one of many amino acids that comprise a protein molecules 122. Lysine, has a free amine group 120 that will attach to the surface via an amide bond. The molecules designated as 122 in FIG. 9D will be treated as ligands in the following discussion concerning kinetic binding measurements. Preferably, the surface concentration of ligand molecules 122 as shown in FIG. 10 is low enough to allow ample space between receptor molecules. The space enables analyte molecules 124 to interact, or bind with ligand molecules 122 without any residual interaction with neighboring ligand molecules 122.

The surface concentration of ligand molecules 122 is controlled by providing a low concentration of ligand molecules 122 in the buffer solution flowing through flow channel 61, and by measuring the optical path difference in real-time in order to provide information regarding the time to terminate the ligand molecule 122 immobilization process. After the ligand molecules 122 are immobilized, the remaining reactive binding sites 506 are capped, or rendered unreactive, by flowing a concentration of a small molecule such as ethanolamine or Tris to block any reactive NHS groups, so that binding of analyte molecules 124 will only occur with ligand molecules.

e) Binding Step

The chemistry associated with the actual binding step is demonstrated cartoon-like in FIG. 9E. Analyte molecules 124 diffusing down from continuous flow are attracted to ligands 122 as indicated at 126 in FIG. 9E and is bound as shown at 127.

f) Disassociation Step

For many binding reactions the binding is weak and temporary and after the analyte flow has been replaced with buffer flow the analyte molecules will disassociate from the ligand molecules. The amount of time necessary to remove analyte molecules completely from the surface depends on the binding strength of the biomolecular interaction between the ligand and the analyte. Ligand/analyte pairs that have a weak interaction can disassociate from each other very quickly and a buffer rinse may remove all the analyte present during a five minute rinse step. A strong ligand/analyte interaction can disassociate at a very slow rate and by introducing a buffer step only a few analyte molecules are rinsed off during a five minute rinse step.

g) Regeneration Step

The disassociation step can be and often is accelerated by a regeneration step in which a weak acid solution is flowed over the observation region. The weak acid decreases the pH of the solution and protonates the binding site between the ligand and analyte thus removing the analyte from the ligand. The regeneration step is always followed by a buffer rinse of the surface to bring the solution within the observation region back to a neutral pH.

Optical Path Differences

Figure 4:
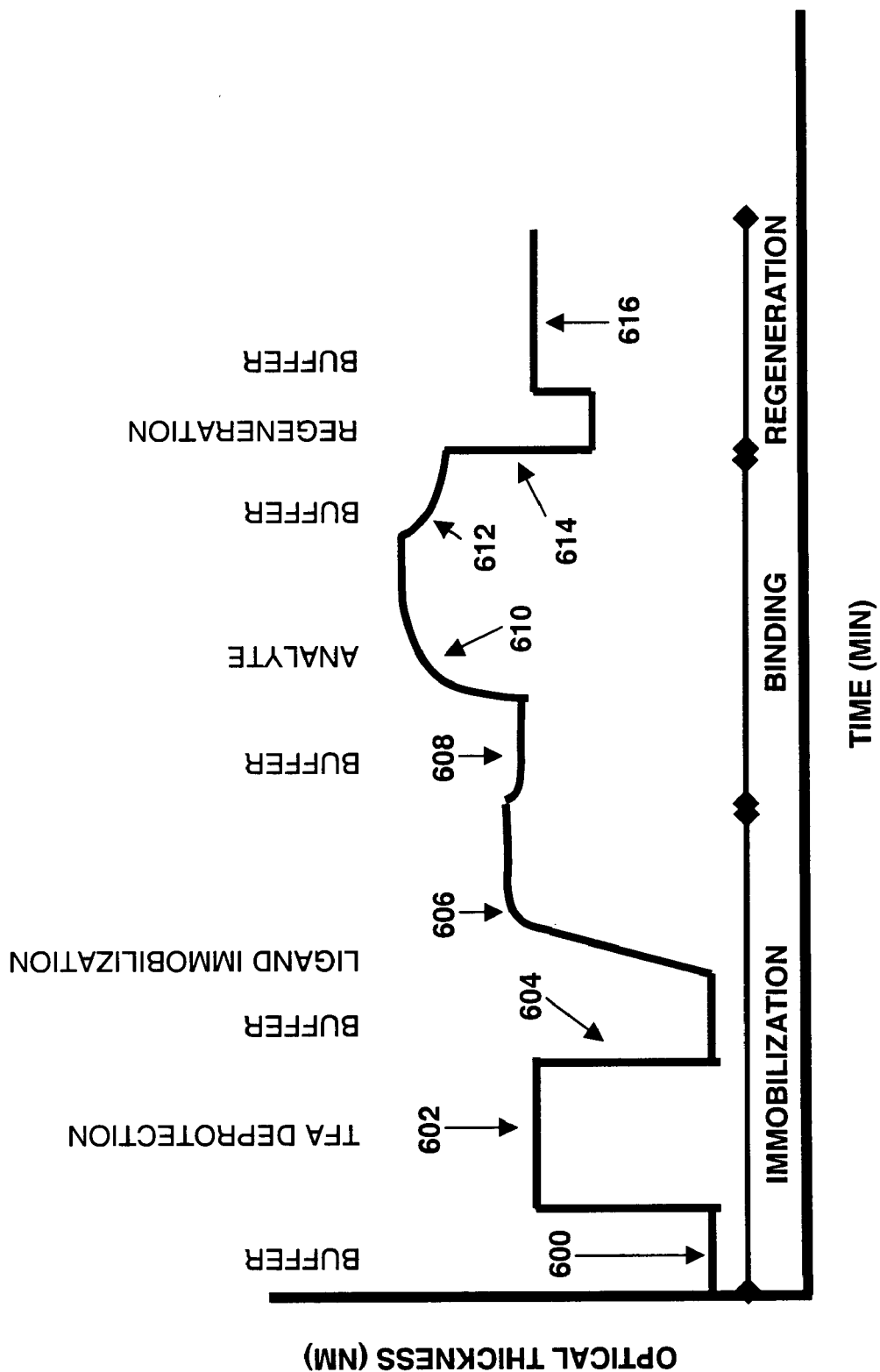
FIG. 4 is a graph showing variations in optical path difference of an interaction region with various molecule containing fluids occupying the interaction region.
Figure 5:
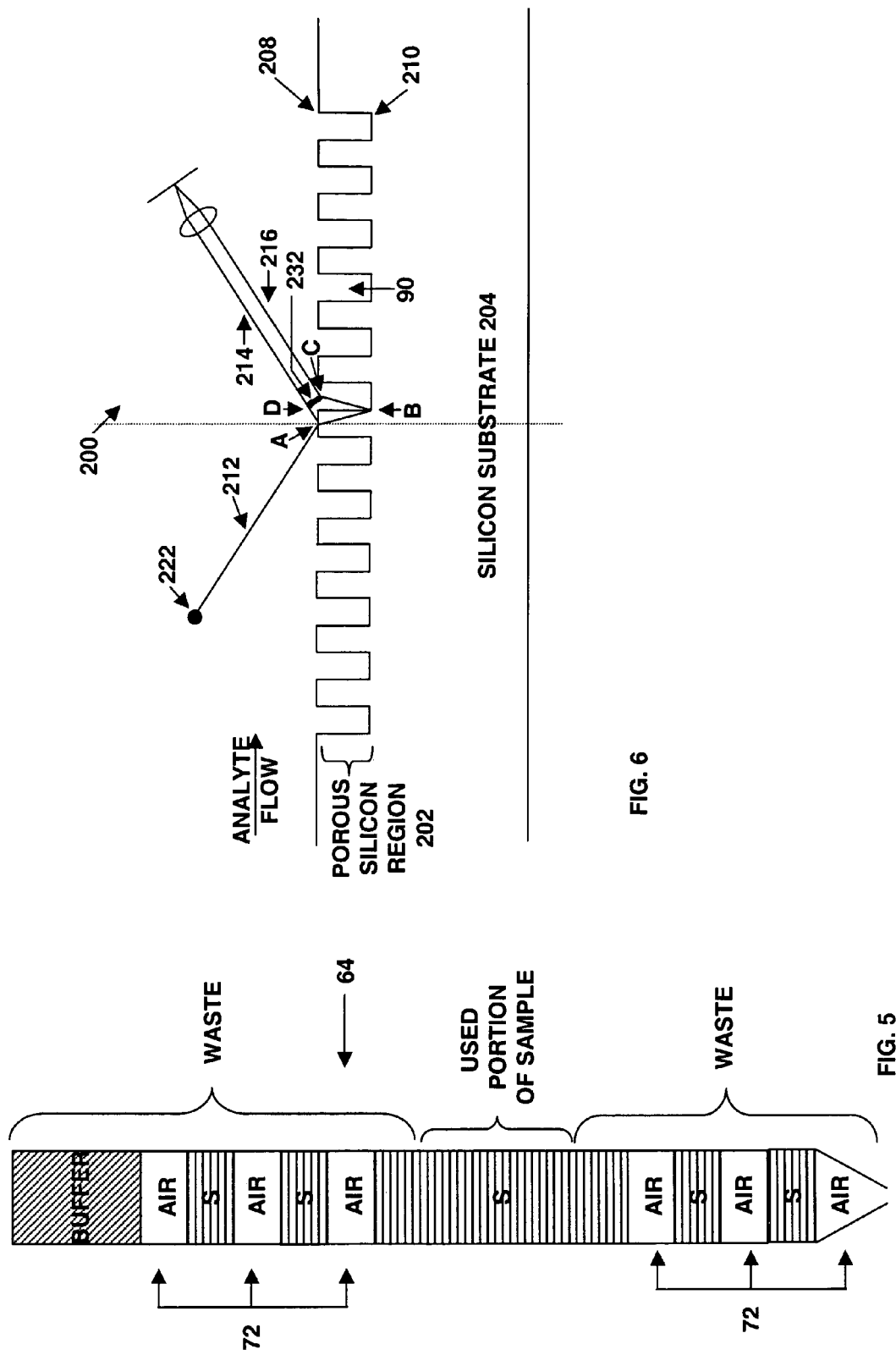
FIG. 5 is a drawing showing a technique for avoiding diffusion between sample and buffer.

FIG. 4 is a graph providing a qualitative description of changes in optical path differences that may be measured using the equipment and techniques described above. Specifically this chart corresponds to Steps c-g with reference to FIGS. 9C-9F as described in the proceeding section. The first two steps (a and b) are performed separately from the FIG. 1 device. When cartridge 42 is installed in unit 13 and buffer flow is initiated the measured optical path difference OPD would appear as shown at 600 in FIG. 4.

Additions of Trifluoroacetic acid (TFA) to remove the protective t-boc group 106 as shown in FIG. 9C will increase the index of refraction in the observation region and show up as an increase in the apparent OPD as shown at 602 but once the flow of buffer removes the TFA from the observation region, the OPD will decrease as shown at 604. The attachment of ligands, explained in step d and FIG. 9D appears as a gradual increase in the OPD (as shown at 606) as the ligands are covalently attached. When a sufficient quantity of ligands has been immobilized to the surface via the linker molecules the flow of ligands is stopped and replaced by a buffer flow resulting in a slight decrease in the OPD 608 as unattached ligand molecules flow out of the observation region with the buffer flow. The most important steps of the process then begin with the addition of the analyte as shown in FIG. 9E and as the analytes become bound to the ligands the measured OPD will increase as indicated at 610 in FIG. 4. The rate of increase and the equilibrium condition of the reaction are both important parameters with respect to a very large number of binding reactions that can be monitored with the present invention. Typically, after sufficient time has passed for the OPD to approach equilibrium as shown in FIG. 4, the analyte flow is replaced with buffer flow and the disassociation rate is monitored as shown at 612. After sufficient data has been collected to determine the disassociation rate, the unit can be "regenerated" as described in the previous section with a weak acid solution with the effect shown at 614 in FIG. 4. Then restoration of the buffer flow restores the observation region to the condition shown at 606 as shown at 616. The unit is then ready for another experiment.

Ligand—Analyte Binding Experiments For Device Demonstration

The embodiment of the present invention shown in FIG. 1 may be used to test binding reactions of a very large number of molecules covering a wide range of reaction rates. Applicants have provided below four examples of ligand—analyte combinations that may be used to test the performance of this embodiment and to assure that it is functioning properly.

Weak Interaction—DNSA/CAII

For a weak interaction providing kinetics and equilibrium data, a good test is to use 5-dimethyl-amino-1-naphthalene-sulfonamide (DNSA) as the ligand and carbonic anhydrase isozyme II (CAII) as the analyte. Both proteins are available from Sigma Chemical with offices in St. Louis, Mo.

Fast On Rate, Moderate Off Rate (GFP/mAb)

For a fast on rate and a moderate off rate, a good test set would be to use green fluorescent protein (GFP) as the ligand and monoclonal antibody (mAb) as the analyte. Both of these molecules are also available from Sigma Chemical.

Moderate On Rate, Slow Off Rate (DNA/DNA)

A good test for proteins with a moderate on rate and a slow off rate is to use DNA for both ligand and analyte. Reaction rates of these molecules are very well known. These molecules can be obtained from Sigma-Genosys, offices in The Woodlands, Tex.

Sensitivity of Analyte Assay (Anti-IgH/Human IgG)

To determine the effectiveness of the device at checking the sensitivity of the analyte assay a good ligand analyte combination is Anti Immunoglobulin G (Anti-IgG) for the ligand and Human Immunoglobulin G (Human IgG) for the analyte. Both can be purchased from Pierce Chemical, with offices in Rockford, Ill.

TSH, Anti-TSH

Another ligand-analyte example is the Human Thyroid Stimulating Hormone (TSH) and the anti-TSH antibody. This example is described in detail in a subsequent reactor of this specification.

Software Control and Analysis

The preferred embodiment shown in FIG. 1 includes a software control and analysis subsystem that automatically controls the timing sequence of fluid delivery of ligand and analyte molecules, monitors and/or records spectral patterns versus optical wavelength, computes optical path difference (OPD) measurements from the spectral patterns, and stores in a personal computer the OPD data as a function time. This data represents kinetic binding data. Further analysis software calculates binding rate constants, $k_{on}$ and $k_{off}$, from groups of measured kinetic binding data. This software is based on a kinetic binding measurement model described below.

Mathematical Model

Figure 6:
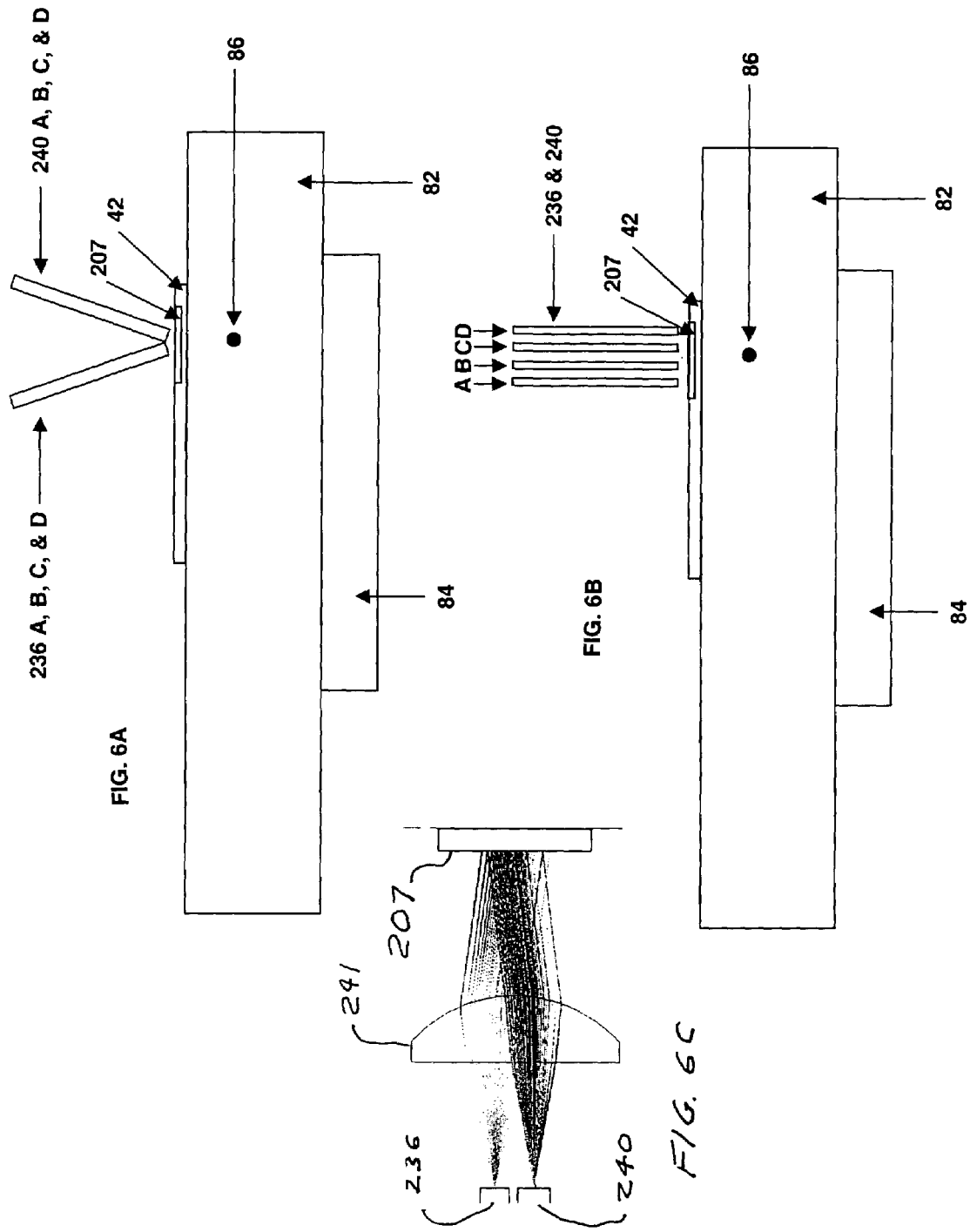
FIG. 6 is a drawing describing a technique for monitoring changes in optical path difference in an interaction region.

FIG. 6 is a sketch showing interferometric features of the present invention which will be referred to in order to explain some of the concepts on which this invention is based. (Some of these concepts are also explained at pages 295-309 in Optics by Eugene Hecht and Alfred Zajac, Addison Wesley.) Light beam (wavelength $\lambda$) from point source 222 is incident on a porous silicon interaction volume 202 in silicon substrate 204 at incident angle $\theta_i$. The amplitude of electric field $E_0(\lambda)$ of beam 212 is split at the first interface 208 at the top of porous silicon region 202 into two beams 214 and 216. The second beam 216 travels the path $\overline{AB}$, is partially reflected at the second interface 210 at the bottom of region 202, and travels the path $\overline{BC}$ to point C. The first beam 214 travels the path $\overline{AD}$ and recombines as a linear superposition with the second 216 along the constant phase wavefront $\overline{DC}$ 232. The optical path difference (OPD) of the interferometer is defined as $$OPD = n_r(ps)[(\overline{AB}) + (\overline{BC})] - n_r(\text{buffer})(\overline{AD}) \quad (1)$$

The corresponding optical phase difference associated with the OPD is given by $$\delta = \frac{4\pi L}{\lambda}(n_r^2(ps) - n_r^2(\text{buffer})\sin^2\theta_i)^{\frac{1}{2}} + \delta_o \quad (2)$$

where $\delta_0$ is a phase shift that occurs upon reflection of the second beam 216 at the second interface 210. The combined reflected beam 214 and 216 are subject to constructive or destructive interference that depends on the optical phase difference $\delta$. (As described below, white light is used in preferred embodiments, which is equivalent to a very large number of overlapping monochromatic beams.) Total constructive interference of beams 214 and 216 occurs when $$\delta = 2\pi m \quad (3)$$

where m is an integer. Thus, the interaction volume 202 functions as a porous silicon interferometer. The OPD can be expressed as $$OPD = 2L(n_r^2(ps) - n_r^2(\text{buffer})\sin^2\theta_i)^{\frac{1}{2}} + \frac{\delta_o \lambda}{2\pi} \quad (4)$$

The key optical features of the porous silicon interferometer are 1) the optical quality, partially reflective interfaces 208 and 210, and 2) the high degree of parallelism between the interfaces. The optical quality of the porous silicon optical interferometer 200 is determined primarily by the relatively small pore diameters (80-120 nm) compared to the wavelengths $\lambda$ of the incident light (450-900 nm). The high degree of parallelism between interfaces 208 and 210 occurs as a natural spatial uniformity in the depth L of porous silicon interaction volume 202, as a result of the etching process.

Optical Layout

Figure 16:
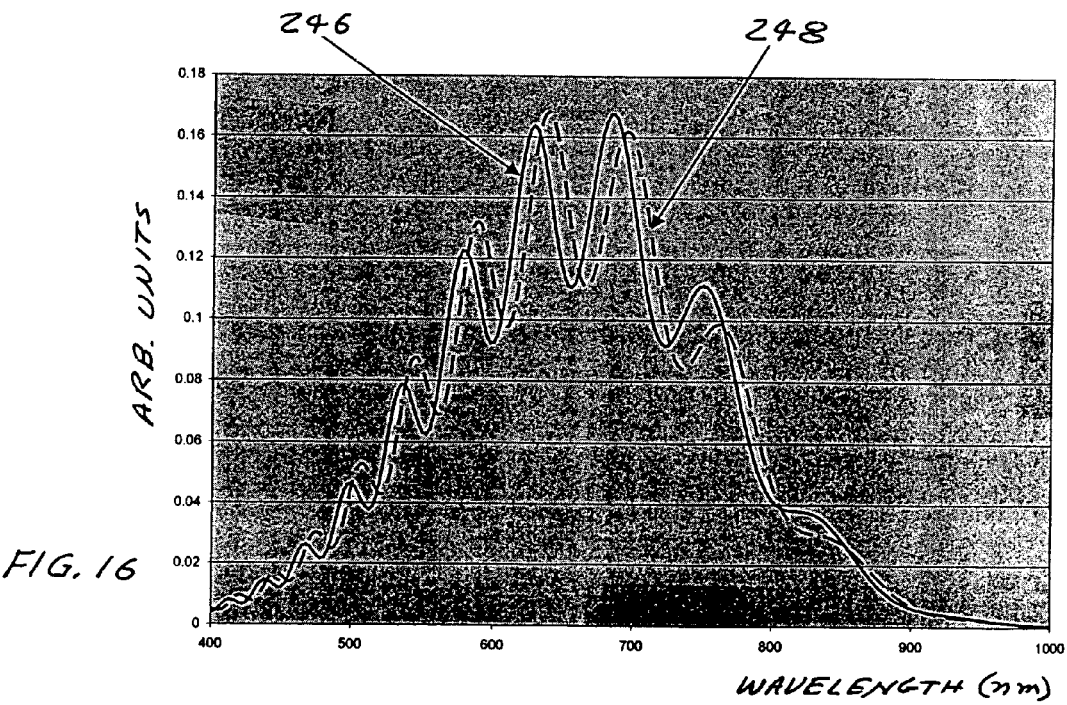
FIGS. 16-21 are graphs explaining features of a mathematic model supporting embodiments of the present invention.

FIGS. 6A, 6B, and 6C display a preferred optical measurement layout. White light (450-900 nm) from a tungsten halogen lamp (preferably Ocean Optics Model LS-LL-1, shown at 222 in FIG. 1) is used to generate a simultaneous plurality of monochromatic light beams. The white light from lamp 222 is directed via a first fiber optic to an optical manifold where the light is divided into four optical fibers 236. One of these fibers is shown in FIG. 6C. Light from these four optical fibers is directed by lens 241 through optical window 207 as shown in FIG. 6A on to incident on the porous silicon interaction volume 202 at angle of incidence $\theta_i$ as shown in FIG. 15A. For each of the four beams, light reflected from the interfaces 208 and 210 is directed back through lens 241 and through a second 400 micron diameter fiberoptic 240 as shown in FIG. 6C to spectrometer 71 (preferably Tech5Helma Model MMS-1). FIG. 16 is a graphical representation of a mathematical model for a typical interference pattern 246 produced by the porous silicon interferometer that is measured as a function of light intensity versus optical wavelength $\lambda$ by a linear photodiode array (preferably Hamamatsu Model 3904) incorporated at the optical output of the spectrometer. The interference pattern is unique for a given optical path difference. In preferred embodiments a change in the refractive index $n_r(ps)$ of the porous silicon interaction volume 202 results in a change in the optical path difference that is measured as a change of the entire interference pattern 243 versus wavelength $\lambda$, as displayed in FIG. 16. It is assumed, in preferred embodiments that the optical path length corresponding to path $\overline{AD}$ remains constant, thus acting as the reference path of the optical interferometer.

The model for the porous silicon interaction volume 202, displayed in FIG. 15 and consists of a plurality of cylindrical pores, or holes, 90 with pore diameter d and pore depth L. The actual interaction region 202 consists of a distribution of pore diameters centered around an average pore diameter d. The typical full width half maximum of the pore diameter distribution is approximately d/4. However, the actual pore depth distribution is tightly centered around the average depth L with the full width half maximum of the pore depth distribution approximately equal to the pore radius d/2. At the start of each test, the pores 90 are typically filled with buffer solution with index of refraction $n_r(buffer)$ and bulk silicon 204 that surrounds the pores 90 has an index of refraction $n_r(silicon)$.

The complex index of refraction $n(ps)=n_r(ps)+in_i(ps)$ of the interaction volume 202 includes real and imaginary components. The imaginary component $n_i(ps)$ is related to absorption of light and the real component $n_r(ps)$ is related to changes in the speed of light, in the porous silicon interaction volume 202. The preferred embodiment of the optical biosensor exploits the measurement of changes in the real part $n_r(ps)$ of the index of refraction of the interaction volume 202, which is modeled, using the effective medium approximation, as a volumetric average of the real part of the index of refraction $n_r(silicon)$ of the bulk silicon and the real part of the index of refraction $n_r(med)$ of the material, or medium, filling the pores 50, $$n_r(ps)=(1-P)n_r(silicon)+Pn_r(med) \qquad \text{Eq. (5)}$$

The porosity P is defined as the volume of the pores 90 divided by the total volume of the interaction volume 202. The pore diameter d, pore depth L, and porosity P are achieved by control of the porous silicon etching parameters including etching current density, etching time, hydrofluoric acid concentration, and conductivity of the bulk silicon. Typical porosities P=0.80–0.95 are used for protein binding measurements. If we use parameters $n_r(silicon)=3.7$, $n_r(med)=n_r(buffer)=1.33$, and P=0.80, then equation (5) gives $n_r(ps)=1.804$.

In the preferred embodiment, the invention is used to measure the surface concentration of a monolayer 93 of molecules (ligands and analytes) that are attached to the cylindrical walls of pores 90. We will sometimes in this analysis refer to this monolayer of V molecules as a monolayer of proteins. The index of refraction $n_r(med)$ of pores 90 changes slightly due to attachment, via linker chemistry, of ligand molecules B to the walls of pores 90. The index of refraction $n_r(med)$ of pores 90 also changes slightly due to the binding of analyte molecules 124 to the ligand molecules 122 attached to the walls of pores 90. The change in the index of refraction $n_r(med)$ of pores 90 results in a change in the index of refraction $n_r(ps)$ of the PS interaction volume 2, as described by equation (5). The index of refraction $n_r(med)$ of the medium filling the pores is modeled, using the effective medium approximation, as a volumetric average of the index of refraction $n_r(buffer)$ of the buffer solution and the index of refraction $n_r(protein)$ of the protein monolayer 93 on the walls of pores 90, $$n_r(med) = \frac{V_{buff}}{V_{med}}n_r(buffer) + \frac{V_{prot}}{V_{med}}n_r(protein). \qquad \text{Eq. (6)}$$

where $V_{med} = \frac{\pi d^2 L}{4} = V_{buff} + V_{prot}$ is the total volume of a single pore 90.

The volume of the protein monolayer layer 93, displayed in FIG. 4, is modeled as $$V_{prot} = \left[\frac{\pi d^2 L}{4} - \frac{\pi(d-2\rho)^2 L}{4}\right]F. \qquad \text{Eq. (7)}$$

where $\rho$ is the thickness of the protein monolayer 93. The variable F (0<F<1) accounts for the fractional surface coverage of the protein monolayer 93. Also, the model assumes that the volumetric coverage of the bottom of pore 90 is negligible compared to the volumetric coverage of the cylindrical pore wall. The volume of the buffer is then $$V_{buff} = V_{med} - V_{prot} = \frac{\pi d^2 L}{4} - \left[\frac{\pi d^2 L}{4} - \frac{\pi(d-2\rho)^2 L}{4}\right]F \qquad \text{Eq. (8)}$$

Inserting equations (6) through (8) into equation (5) gives $$n_r(ps) = (1-P)n_r(silicon) + Pn_r(buffer) + P\frac{4\rho}{d}\left(1-\frac{\rho}{d}\right)\Delta n_r F \qquad \text{Eq. (9)}$$

where $\Delta n_r = n_r(protein) - n_r(buffer)$. The typical index of refraction for a 50,000 to 150,000 Dalton protein is $n_r(protein)=1.42$. For a typical protein monolayer thickness $\rho$ and pore diameter d, we can approximate $$1 - \frac{\rho}{d} \approx 1.$$

If we use parameters $n_r(silicon)=3.7$, $n_r(buffer)=1.33$, and P=0.80, d=100 nm, then equation (9) gives $$n_r(ps)=1.804+(0.00288 \text{ nm}^{-1})F\rho \qquad \text{Eq. (10)}$$

Figure 17A:
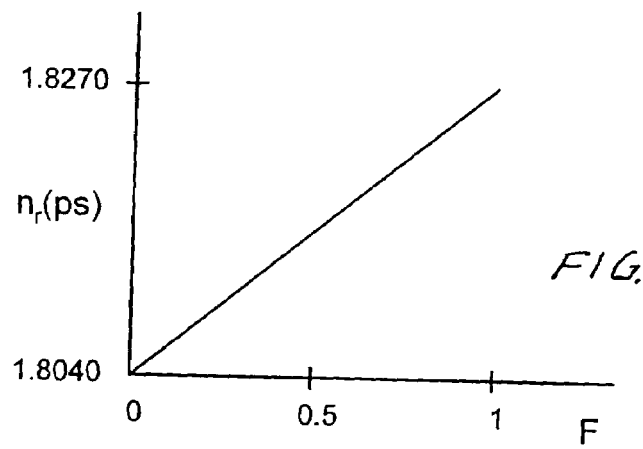

FIG. 17A displays $n_r(ps)$ versus fractional surface coverage F for 150,000 Dalton protein molecules ($\rho$=8 nm).

The invention measures changes in OPD, given by equation (4), due to changes in the index of refraction $n_r(ps)$ of the interaction volume 202. Combining equation (9) with equation (4) gives $$OPD = 2L\left[(1-P)n_r(\text{silicon}) + Pn_r(\text{buffer}) + \right.$$

$$\left. P\frac{4\Delta n_r}{d}\left(1-\frac{\rho}{d}\right)F\rho\right)^2 - n_r^2(\text{buffer})\sin^2\theta_i\right]^{\frac{1}{2}} \frac{\delta_o\lambda}{2\pi} \qquad \text{Eq. (11)}$$

Figure 17B:
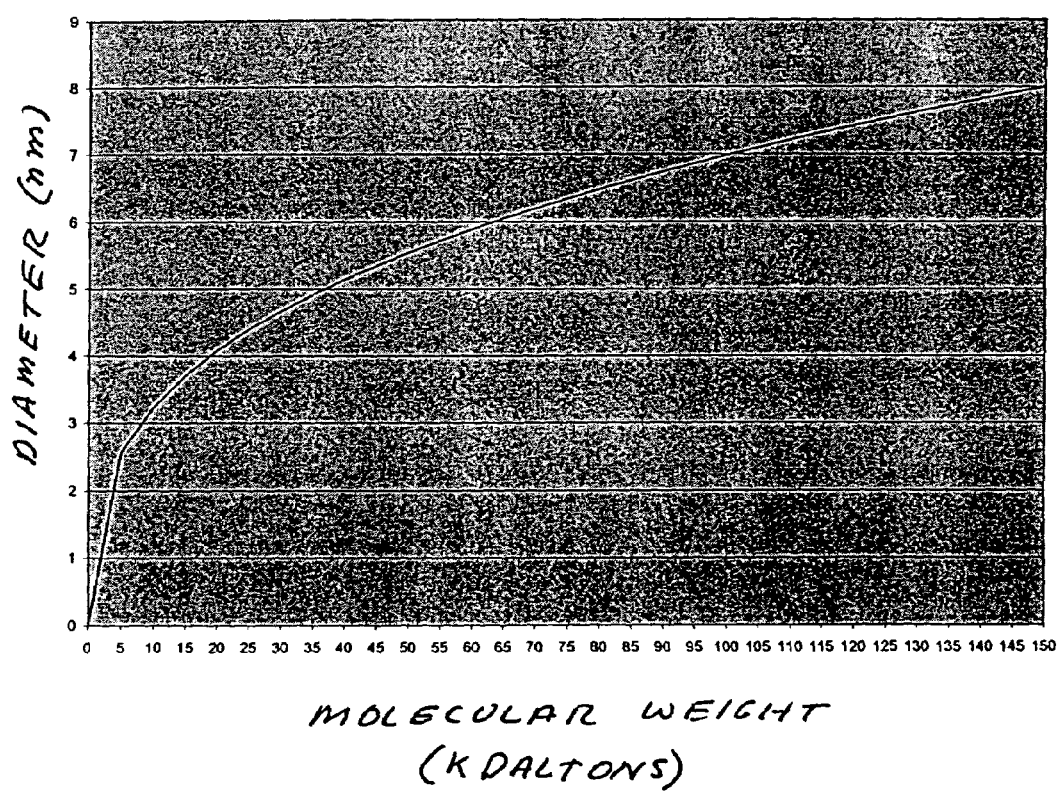

The fractional surface coverage F is related to the surface concentration (dimensions pg/mm²) of proteins on the pore walls. A protein of mass M is modeled as a cylinder with diameter ρ and height ρ, given by $$\rho = \rho_o\left(\frac{M}{M_o}\right)^{\frac{1}{3}}. \qquad \text{Eq. (12)}$$

where $\rho_0$=8 nm and $M_0$=150,000 Daltons. Equation (12), plotted in FIG. 17B, shows that for the diameters of the majority of proteins examined in kinetic binding experiments (typically 30,000 to 150,000 Daltons) are in the ρ=5-8 nm range.

Figure 18:
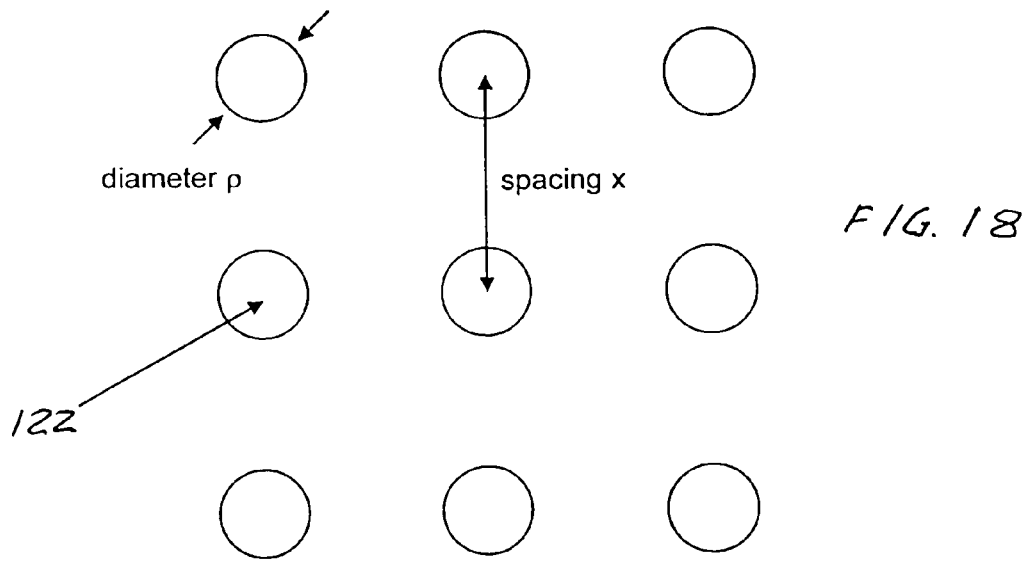

FIG. 18 displays a model for the surface coverage of ligands 122 on the walls of pores 90. The surface concentration of proteins ligands is given by $$\sigma = M/Ax^2 \text{ (units pg/mm}^2\text{)} \qquad \text{Eq. (13)}$$

where M is the molecular weight of the protein (Daltons or g/mol), and A=6.022×10²³ (molecules/mol) is Avogadro's number. Although the proteins 122 are distributed somewhat randomly on the pore walls, the average distance between each protein molecules is x. The model assumes that the proteins 122 are arranged in a regular grid pattern, as displayed in FIG. 18. The fractional surface coverage F is then given by $$F = (\rho/x)^2, \qquad \text{Eq. (14)}$$

defined so that F=1 when ρ=x. By combining equations (9), (12)-(14), we can relate the OPD to the surface concentration density σ (units pg/mm²) as $$OPD = 2L\left[(1-P)n_r(\text{silicon}) + Pn_r(\text{buffer}) + \right.$$

$$\left. P\frac{4\Delta n_r}{d}\left(1-\frac{\rho}{d}\right)\frac{\rho_o}{M_o}A\sigma\right)^2 - n_r^2(\text{buffer})\sin^2\theta_i\right]^{\frac{1}{2}} + \frac{\delta_o\lambda}{2\pi} \qquad \text{Eq. (15)}$$

For the preferred operational parameters listed previously, equation (15) gives $$OPD = 2L\left[\left(1.804 + \left(5.92E - 6\frac{\text{mm}^2}{\text{pg}}\right)\sigma\right)^2 - 1.769\sin^2\theta_i\right]^{\frac{1}{2}} + \frac{\delta_o\lambda}{2\pi}. \qquad \text{Eq. (16)}$$

The resolution of the optical measurement is a key feature of the invention. The present prototype has a 1 part per million resolution in the measurement of OPD, defined as the root mean squared (rms) variation in the baseline OPD divided by the measured OPD. A typical OPD is approximately 6000 nanometers, so the resolution of the device is approximately ΔOPD=(10⁻⁶)(6000 nanometers)=0.006 nanometers or 6 picometers. The high degree of resolution is provided by two key factors, 1) the use of very high optical signal averaging to increase the signal-to-noise ratio (SNR) of the measured interference fringe patterns, and 2) the use of novel computational fringe fitting algorithms that most accurately computes the OPD from the interference fringe patterns 246.

The optical signal averaging is accomplished by the use of a very deep well linear photodiode array (Hamamatsu 3904; 256 pixels, 156 million photoelectrons full well capacity) for the linear detector in the spectrometer. In addition, very fast frame rate acquisition methods are used that currently record one hundred frames of interference fringe data every second and sum the one hundred frames pixel-by-pixel to provide an interference fringe pattern versus wavelength every second with a very high SNR. For example, each pixel value in the very high SNR interference fringe pattern represents approximately (156 million photoelectrons/2)(100)=8×10⁹ electrons. The primary noise source for this measurement is photoelectron shot noise; the rms value for this noise is the square root of the signal, $\sqrt{8\times 10^9 \text{electrons}}$=9×10⁴ electrons. The SNR of the fringe pattern is then 8×10⁹ electrons/9×10⁴ electrons=90,000.

Correlation Method

The preferred embodiment uses a special correlation method for calculation of OPD from the measured interference fringe patterns, as described here. The model for the measured interference fringe pattern is given by $$I_r(\lambda) = I_{ro}(\lambda)[1 - M\cos(2\pi OPD/\lambda)] \qquad \text{Eq. (17)}$$

where M is the modulation index and $$I_{ro}(\lambda) = \frac{1}{\sqrt{2\pi}\,\sigma}\exp(-(\lambda-\lambda_o)^2/2\beta^2) \qquad \text{Eq. (18)}$$

is a normalized Gaussian envelope function. The actual envelope function is determined by the spectral bandwidth of the light source, spectrometer, and linear photodiode array, as well as the wavelength dependent reflection properties of the interaction volume 202. FIG. 16 shows equations (17) and (18) (246 and 248) with operational parameters OPD=7216 nm, $\lambda_o$=660 nm, β=100 nm, and M=0.2. The measured interference fringe pattern is correlated to a test fringe pattern $$I_r(X;\lambda) = I_{ro}(\lambda)[1 - M\cos(2\pi X/\lambda)] \qquad \text{Eq. (19)}$$

where X is a varying test optical thickness, using the correlation integral $$C(X) = \frac{1}{M}\int_{-\infty}^{\infty} d\lambda\{I_T(X;\lambda) - I_{ro}(\lambda)\}\{I_r(\lambda) - I_{ro}(\lambda)\} \qquad \text{Eq. (20)}$$

Figure 19:
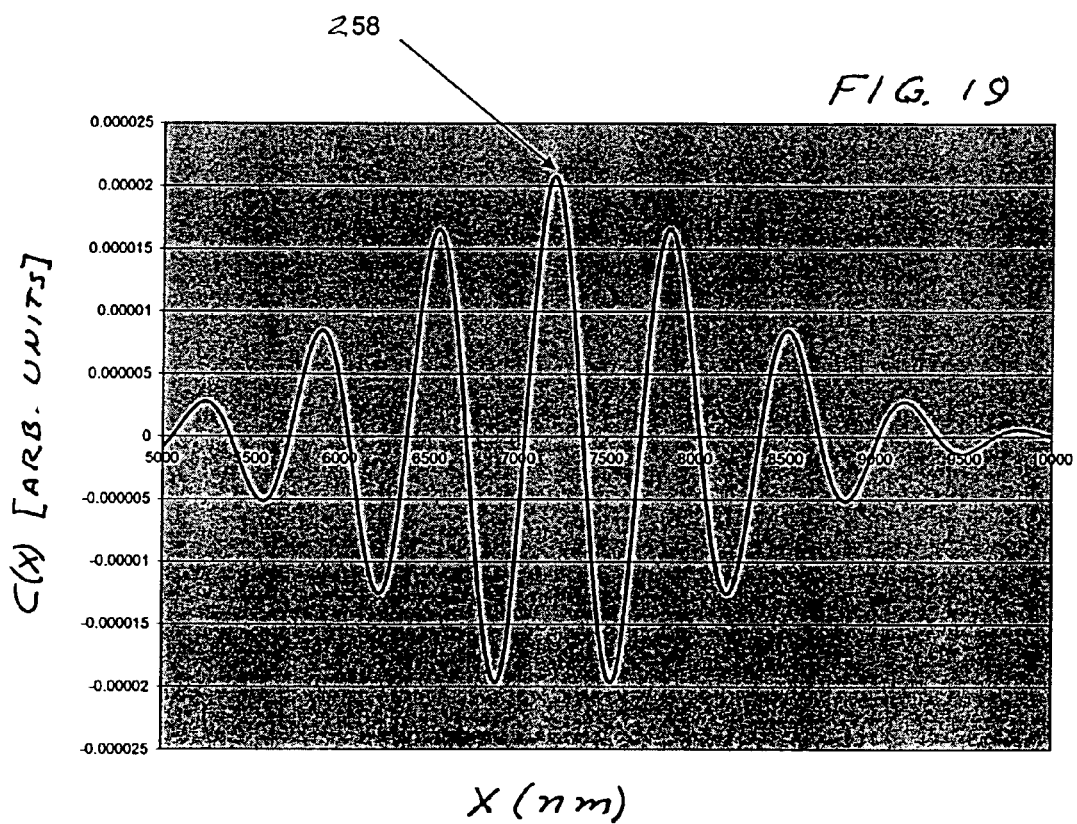

FIG. 19 shows the correlation integral C(X) versus X for the model of a typical interference fringe pattern 246 given by equation (17). The OPD is calculated from the equation (20) as the value of X corresponding to the peak 258 of C(X). This value of X is precisely determined by the locating the zero crossing of the first derivative of C(X) with respect to X, or C'(X).

Figure 20:
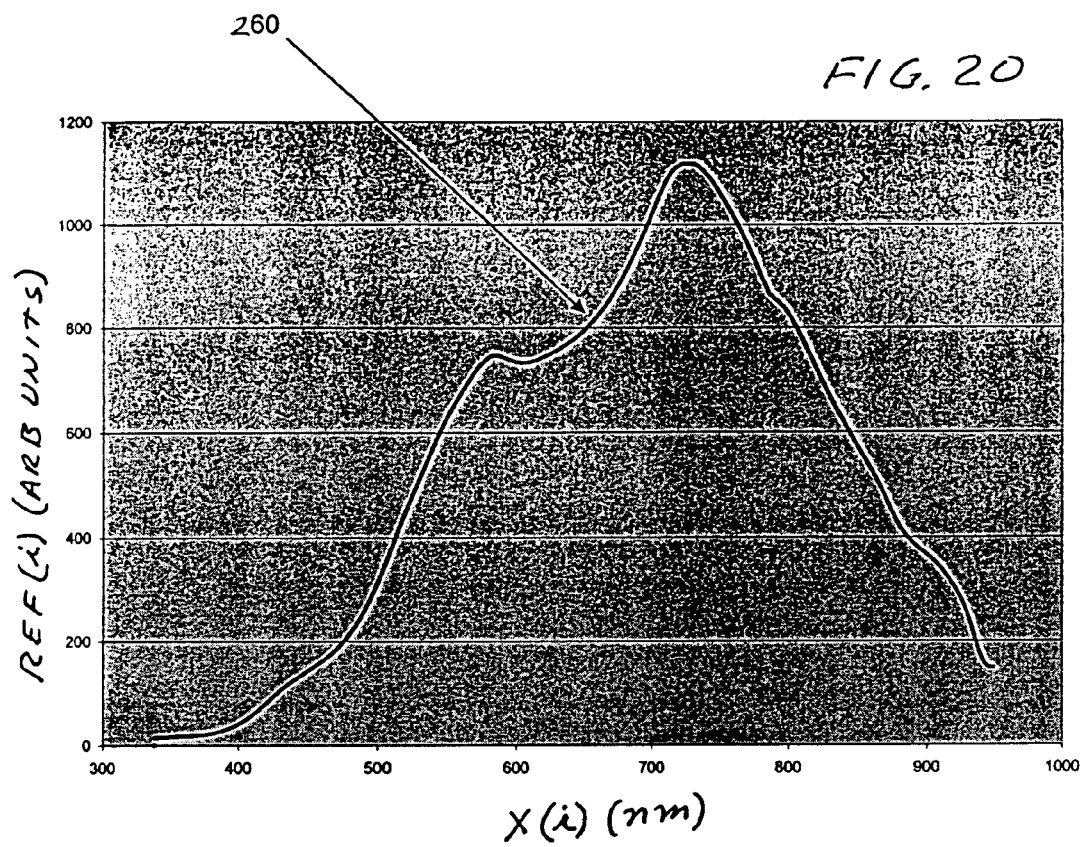

The exact procedure for the acquisition of the interference fringe patterns and calculation of the OPD is given here:

1) Acquire reference pattern—FIG. 20 displays a typical reference pattern 260 versus optical wavelength that is acquired from the invention. This pattern is acquired by replacing the interaction volume 202 with a non-porous silicon chip in order to accurately record the envelope optical response function (i.e. without interference fringes), modeled by equation (18), of the light source, spectrometer, and linear photodiode array. The data {λ[i], RawRef[i]}; (i=1=0, Nlambda) in FIG. 20 represents a summation of multiple frames of pixel data in order to provide greater signal-to-noise by signal averaging the shot noise of the incident photons. The reference data displayed in FIG. 20 is acquired once and is stored in a look-up table for use in the calculation of the OPD.

Figure 21:
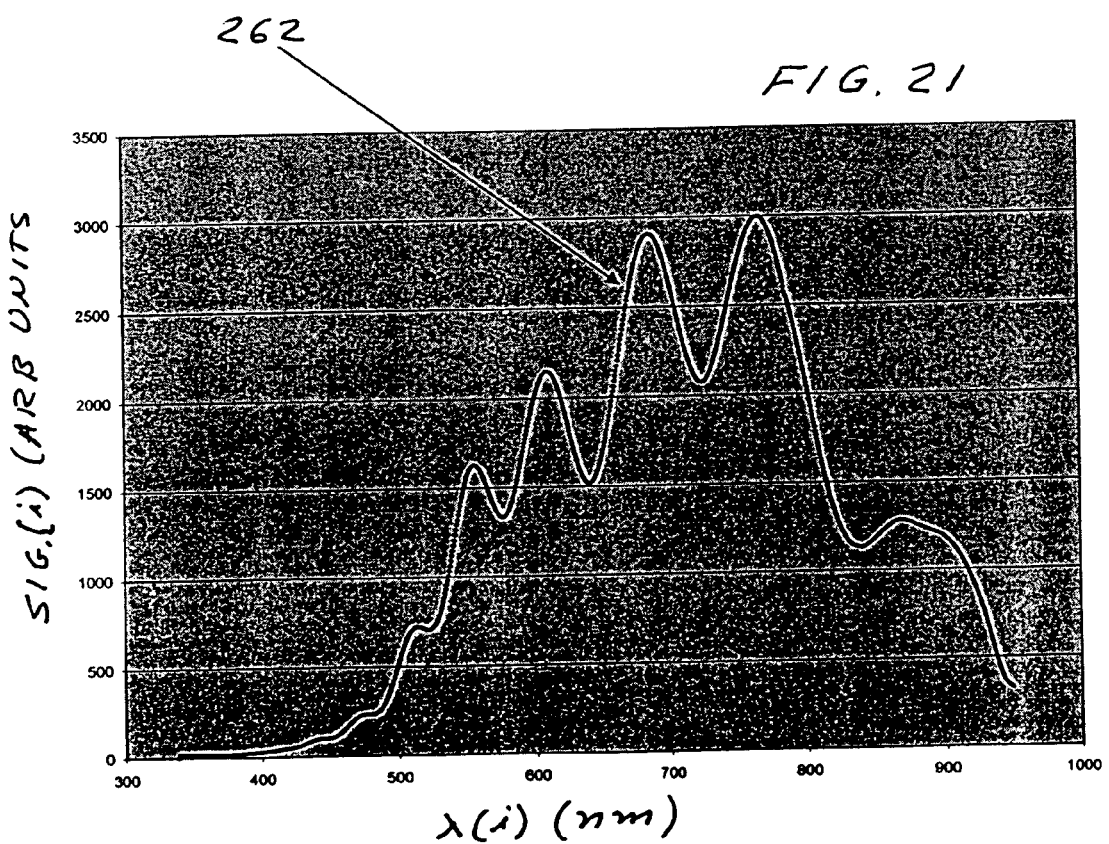

2) Acquire interference fringe pattern—FIG. 21 displays a typical interference fringe pattern versus optical wavelength 262 that is acquired from the interaction volume 202. Each data point in FIG. 21 represents a summation of a plurality of frames, typically one hundred, of pixel data in order to provide greater a signal-to-noise by signal averaging the shot noise of the incident photons. The data {λ[i], RawSig[i]};(i=0, Nlambda) displayed in FIG. 21 is a summation of one hundred frames, summed together, every second. The value Nlambda=256 is the number of pixels in the photodiode detector array.

3) Normalize interference fringe pattern and reference pattern—The acquired data is normalized as such:

$$Sig[i] = \left(\sum_{i=0}^{Nlambda} \Delta\lambda[i] RawSig[i]\right)^{-1} RawSig[i] \quad \text{Eq. (21)}$$

and $$Ref[i] = \left(\sum_{i=0}^{Nlambda} \Delta[i] RawRef[i]\right)^{-1} RawRef[i] \quad \text{Eq. (22)}$$

4) Calculate correlation function—The correlation function given in equation (20) is calculated using the experimental data $$I_r(\lambda) - I_{ro}(\lambda) = Sig[i] - Ref[i] \quad \text{Eq. (23)}$$

to give $$C(X[j]) = -\sum_{i=0}^{NLambda} \Delta\lambda[i](Sig[i] - Ref[i])Ref[i]\cos\left(\frac{2\pi X[j]}{\lambda[i]}\right) \quad \text{Eq. (24)}$$

where the value Δλ[i]=λ[i]−λ[i−1] and NTransform<j<NTransform. The preferred calculation method determines the approximate optical path length $X[j_{max}]=OPD_{approx}$ by using a simple numerical search for the maximum value $C(X[j_{max}])$=max value in the range $$\frac{NTransform}{3} < j_{max} < \frac{2NTransform}{3}.$$

The method then uses an interpolation method to find the true peak $X_{pk}$=OPD in the neighborhood of the first determination $X[j_{max}]=OPD_{approx}$. This method iterates to find the zero of the first derivative of the correlation function $$F(X) = \quad \text{Eq. (25)}$$

$$\frac{1}{2\pi}\frac{dC(X)}{dX} = -\sum_{i=0}^{NLambda} \frac{\Delta\lambda[i]}{\lambda[i]}(Sig[i] - Ref[i])Ref[i]\sin\left(\frac{2\pi X}{\lambda[i]}\right)$$

using the Newton-Raphson method. This method provides a sequence of values $\{X_n\}$; (n=0, 1, 2, 3, . . . ) that provide successively more accurate approximations to the root $F(X_n)$=0, using the formula $$X_n = X_{n-1} + \Delta X_n = X_{n-1} + F(X_n)*\left\{\frac{X_n - X_{n-1}}{F(X_{n-1}) - F(X_n)}\right\} \quad \text{Eq. (26)}$$

and the initial starting points $X_1=X[j_{max}]$, $X_0=X[j_{max}]-dX$, $F(X_0)=F(X[j_{max}]-dX)$, and $F(X_1)=F(X[j_{max}])$. The initial value dX is chosen so that the value $X[j_{max}]-dX$ is close to the peak of the correlation function, typically $$dX = \frac{X[j_{max}]}{1000}.$$

Figure 22:
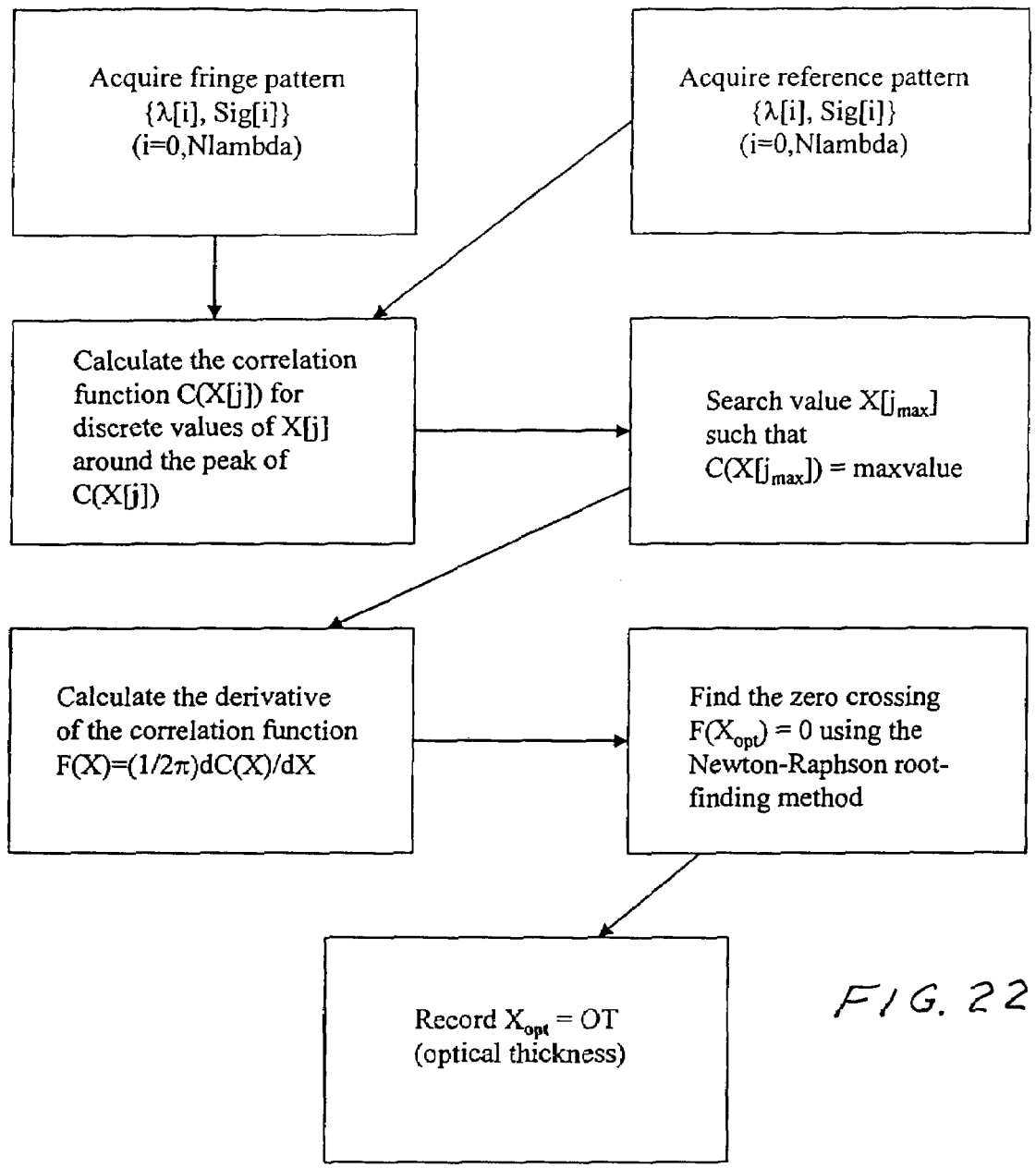
FIG. 22 is a computational flow chart for calculating OPD.

The iteration procedure continues until a desired level of resolution is reached; the higher the level of resolution, the more iterations are required to reach this resolution. However, the stochastic noise in the signal and reference data will ultimately limit the convergence process. We have found that the limit $$|F(X_n)| < C(X[j_{max}])*10^{-9} \quad \text{Eq. (27)}$$

provides adequate resolution. This limit is reached in approximately n=5-10 iterations with relatively smooth functions such as a typical F(X). FIG. 22 shows a computational flow chart for determining the OPD from the interference fringe data.

Alternate embodiments for the fringe fitting algorithm include the cosine transform method and the Fourier transform method. These methods calculate the cosine transform, or the Fourier transform, of the normalized data given in equations (21) and (22), and the locate the peak of the cosine transform, or the Fourier transform, using the Newton-Raphson method.

Dependence of Instrument Resolution on Interferometer Length and Modulation Index The resolution in the calculation of the OPD from the measured fringe pattern 246 is related to the both the OPD and the modulation index M of the fringe pattern. The resolution becomes smaller, or better, as both the OPD increases and the modulation index M increases, as described here. If we add a stochastic noise term to the model, equation 17 is given by $$I_r(\lambda) = I_{ro}(\lambda)[1 - M(2\pi OPD/\lambda)] + N(\lambda) \quad \text{Eq. (28)}$$

and N(λ) is the noise on the spectral fringe pattern. The noise is primarily a combination of photoelectron shot noise and electronic readout noise. The correlation integral C(X) has a well defined peak at the value of $X_{pk} \approx OT$. Equation 28 is combined with equations (17) and (20) to give $$C(X) = M \int_{-\infty}^{\infty} d\lambda I_{ro}^2(\lambda)\cos(2\pi X/\lambda)\cos(2\pi OPD/\lambda) - \int_{-\infty}^{\infty} d\lambda I_{ro}(\lambda)\cos(2\pi X/\lambda)N(\lambda)$$

Eq. (29)

To find the peak where $X_{pk} \approx OPD$, we look for the value of X where the derivative of C(X) is equal to zero.

$$\frac{dC(X)}{dX}\bigg|_{X=X_{pk}} =$$

$$0 = -M\int_{-\infty}^{\infty} d\lambda I_{ro}^2(\lambda)\frac{2\pi}{\lambda}\sin\left(\frac{2\pi X_{pk}}{\lambda}\right)\cos\left(\frac{2\pi OPD}{\lambda}\right) + \int_{-\infty}^{\infty} d\lambda I_{ro}(\lambda)\frac{2\pi}{\lambda}\sin\left(\frac{2\pi X_{pk}}{\lambda}\right)N(\lambda)$$

Eq. (30)

By using the trigonometric relationship $\sin\alpha\cos\beta = \frac{1}{2}[\sin(\alpha+\beta)+\sin(\alpha-\beta)]$, equation 30 can be expressed as $$M\int_{-\infty}^{\infty} d\lambda I_{ro}^2(\lambda)\frac{2\pi}{\lambda}\frac{1}{2}$$
$$\left\{\sin\left[\frac{2\pi}{\lambda}(X_{pk}+OPD)\right]+\sin\left[\frac{2\pi}{\lambda}(X_{pk}-OPD)\right]\right\} =$$
$$\int_{-\infty}^{\infty} d\lambda I_{ro}(\lambda)\frac{2\pi}{\lambda}\sin\left(\frac{2\pi X}{\lambda}\right)N(\lambda).$$

Eq. (31)

The peak of the correlation function is at $X_{pk} \approx OPD$; so $$\sin\left[\frac{2\pi}{\lambda}(X_{pk}-OPD)\right] \approx \frac{2\pi}{\lambda}(X_{pk}-OPD).$$

Equation 31 can then be written as $$X_{pk} = OPD + \frac{\int_{-\infty}^{\infty} d\lambda \frac{I_{ro}(\lambda)}{\lambda}N(\lambda)\sin\left(\frac{2\pi X_{pk}}{\lambda}\right)}{\pi M \int_{-\infty}^{\infty} d\lambda \frac{I_{ro}^2(\lambda)}{\lambda^2}} -$$

$$\frac{\int_{-\infty}^{\infty} d\lambda \frac{I_{ro}^2(\lambda)}{\lambda}\sin\left[\frac{2\pi}{\lambda}(X_{pk}+OPD)\right]}{2\pi \int_{-\infty}^{\infty} d\lambda \frac{I_{ro}(\lambda)}{\lambda^2}}$$

Eq. (32)

or $$X_{pk} = OPD + \epsilon_1 + \epsilon_2.$$

Eq. (33)

The second term $$\epsilon_2 = -\frac{\int_{-\infty}^{\infty} d\lambda \frac{I_{ro}^2(\lambda)}{\lambda}\sin\left[\frac{2\pi}{\lambda}(X_{pk}+OPD)\right]}{2\pi \int_{-\infty}^{\infty} d\lambda \frac{I_{ro}(\lambda)}{\lambda^2}}$$

Eq. (34)

is quite small because the term $$\sin\left[\frac{2\pi}{\lambda}(X_{pk}+OPD)\right]$$

oscillates rapidly between $-1$ and $+1$ and the integral will average to nearly zero. More importantly, this term does not depend on the measurement noise at all, so it will be constant during the kinetic binding curve measurement and will not affect the measurement data since this data is derived from differences of the OPD during the total measurement time.

The magnitude and sign of the first term $$\epsilon_1 = \frac{\int_{-\infty}^{\infty} d\lambda \frac{I_{ro}(\lambda)}{\lambda}N(\lambda)\sin\left(\frac{2\pi X_{pk}}{\lambda}\right)}{\pi M \int_{-\infty}^{\infty} d\lambda \frac{I_{ro}^2(\lambda)}{\lambda^2}}$$

Eq. (35)

will vary from measurement to measurement as the noise $N(\lambda)$ varies randomly.

The resolution of the measurement device can be measured by acquiring a number of independent measurements of the OPD $X_i$ ($i=1, \ldots, p$) while keeping the OPD constant. The resolution is defined as $$\Delta r_{lim} = \frac{\sqrt{\langle \Delta X \rangle^2}}{\langle X \rangle}$$

Eq. (36)

where $$\langle X \rangle = \frac{1}{p}\sum_{i=1}^{p} X_i = OPD + \epsilon_2$$

is the average value of the measurements, and $$\langle \Delta X \rangle^2 = \frac{1}{p}\sum_{i=1}^{p}(X_i - \langle X \rangle)^2 = \frac{1}{p}\sum_{i=1}^{p}[\epsilon_1(i)]^2 = \langle \epsilon_1^2 \rangle$$

Eq. (37)

is the variance of the measurements. The resolution is then calculated by combining equations (35)-(38)

$$\Delta r_{lim} = \frac{1}{\pi MOPD}\left[\int_{-\infty}^{\infty} d\lambda \frac{I_{ro}^2(\lambda)}{\lambda^2}\right]^{-1}\left[\left\langle\left[\int_{-\infty}^{\infty} d\lambda \frac{I_{ro}(\lambda)}{\lambda}N(\lambda)\sin\left(\frac{2\pi OPD}{\lambda}\right)\right]^2\right\rangle\right]^{\frac{1}{2}}$$

Eq. (38)

The integrals in equation (38) are physically realized as sums over the pixels in the photodiode array of the spectrometer. The square of equation (38) can then be expressed as $$(\Delta r_{\lim})^2 = \left(\frac{1}{\pi MOPD}\right)^2 \left[\sum_{i=1}^{R} \Delta\lambda \frac{I_{ro}^2(\lambda_i)}{\lambda_i^2}\right]^{-2} \left\langle \left[\sum_{i=1}^{R} \Delta\lambda \frac{I_{ro}(\lambda_i)}{\lambda_i} N(\lambda_i) \sin\left(\frac{2\pi OPD}{\lambda_i}\right)\right]^2 \right\rangle \quad \text{Eq. (39)}$$

where R is the number of pixels in the photodiode array. The expectation value in equation (39) can also be turned into a sum as shown in equation (37).

$$(\Delta r_{\lim})^2 = \left(\frac{1}{\pi MOPD}\right)^2 \left[\sum_{i=1}^{R} \Delta\lambda \frac{I_{ro}^2(\lambda_i)}{\lambda_i^2}\right]^{-2} \frac{1}{p} \sum_{j=1}^{P} \left[\sum_{i=1}^{R} \Delta\lambda \frac{I_{ro}(\lambda_i)}{\lambda_i} N_j(\lambda_i) \sin\left(\frac{2\pi OPD}{\lambda_i}\right)\right]^2. \quad \text{Eq. (40)}$$

The three sums in equation 40 can be manipulated to give $$(\Delta r_{\lim})^2 = \frac{1}{(\pi MOPD)^2} \left[\sum_{i=1}^{R} \Delta\lambda \frac{I_{ro}^2(\lambda_i)}{\lambda_i^2}\right]^{-2} \frac{1}{p} \sum_{j=1}^{P} \left\{ \sum_{i=1}^{R} \left(\Delta\lambda \frac{I_{ro}(\lambda_i)}{\lambda_i} N_j(\lambda_i) \sin\left(\frac{2\pi OPD}{\lambda_i}\right)\right)^2 + \sum_{m=1}^{R} \sum_{n=1}^{R} \Delta\lambda^2 \frac{I_{ro}(\lambda_m)}{\lambda_m} \frac{I_{ro}(\lambda_n)}{\lambda_n} N_j(\lambda_m) N_j(\lambda_n) \sin\left(\frac{2\pi OPD}{\lambda_m}\right) \sin\left(\frac{2\pi OPD}{\lambda_n}\right) \right\} \quad \text{Eq. (41)}$$

where the second sum includes all terms except when m=n. The primary noise source for the optical biosensor is the shot noise of the photoelectrons incident in the pixels of the linear detector. In this case, the photoelectrons incident on different pixels are uncorrelated and the second sum in equation (41) averages to zero. The shot noise at each pixel is given by Poisson statistics as $$\langle N^2(\lambda_i) \Delta\lambda^2 \rangle = \sum_{j=1}^{P} N_j^2(\lambda_i) \Delta\lambda^2 = I_{ro}(\lambda_i)[1 - M\cos(2\pi OPD/\lambda_i)]\Delta\lambda. \quad \text{Eq. (42)}$$

Combining equations (41) and (42) gives $$(\Delta r_{\lim})^2 = \left(\frac{1}{\pi MOPD}\right)^2 \left[\sum_{i=1}^{R} \Delta\lambda \frac{I_{ro}^2(\lambda_i)}{\lambda_i^2}\right]^{-2} \sum_{i=1}^{R} \Delta\lambda \frac{I_{ro}^3(\lambda_i)}{\lambda_i^2}[1 - M\cos(2\pi OPD/\lambda_i)]\sin^2\left(\frac{2\pi OPD}{\lambda_i}\right) \quad \text{Eq. (43)}$$

Finally, the resolution can be expressed as a function of both the OPD and the modulation index M as $$\Delta r_{\lim} = \frac{1}{OPD}\left[\frac{A}{M^2} - \frac{B}{M}\right]^{1/2} \quad \text{Eq. (44)}$$

with constants A and B given by $$A = \frac{1}{\pi^2}\left[\sum_{i=1}^{R} \Delta\lambda \frac{I_{ro}^2(\lambda_i)}{\lambda_i^2}\right]^{-2} \sum_{i=1}^{R} \Delta\lambda \frac{I_{ro}^3(\lambda_i)}{\lambda_i^2} \sin^2\left(\frac{2\pi OPD}{\lambda_i}\right) \quad \text{Eq. (45)}$$

and $$B = \frac{1}{\pi^2}\left[\sum_{i=1}^{R} \Delta\lambda \frac{I_{ro}^2(\lambda_i)}{\lambda_i^2}\right]^{-2} \sum_{i=1}^{R} \Delta\lambda \frac{I_{ro}^3(\lambda_i)}{\lambda_i^2} \cos(2\pi OPD/\lambda_i)\sin^2\left(\frac{2\pi OPD}{\lambda_i}\right). \quad \text{Eq. (46)}$$

From equations (44)-(46), the resolution becomes smaller, or better, as the optical thickness OPD becomes larger. In addition, the resolution becomes smaller, or better, as the modulation index M becomes larger.

The observed modulation index is related to the diameter d of pores 90 in the interaction volume 202. Smaller pore diameters provide a higher modulation index due to less wavefront distortion of the incident optical beam. The pore diameters, however, need to be large enough to provide space for the molecular interactions to occur, and for unimpeded diffusion of the analyte molecules in and out of the PS interaction volume. In addition, the OPD is linearly related to the depth L of the interaction volume 202, so larger depths L can provide better resolution.

The modulation index M can effectively distinguish between the realm in which larger pore diameters optimizes kinetic binding assays and another realm of smaller pore diameters that is optimal for on/off capture assays because of the better resolution. The mass transport effect can be larger for the on/off capture assays because this technique is not concerned with the temporal dynamics of the binding process. The capture assays are concerned only with the presence or absence of binding.

Kinetic Binding Measurement Model

Figure 11:
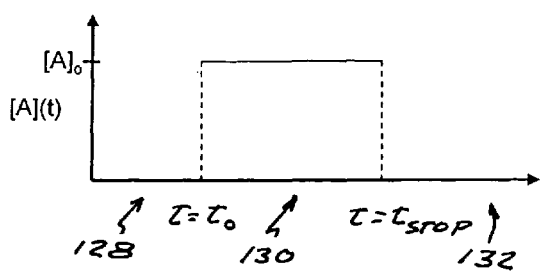
FIG. 11 demonstrates analyte concentrate vs. time in an observation region.
Figure 13:
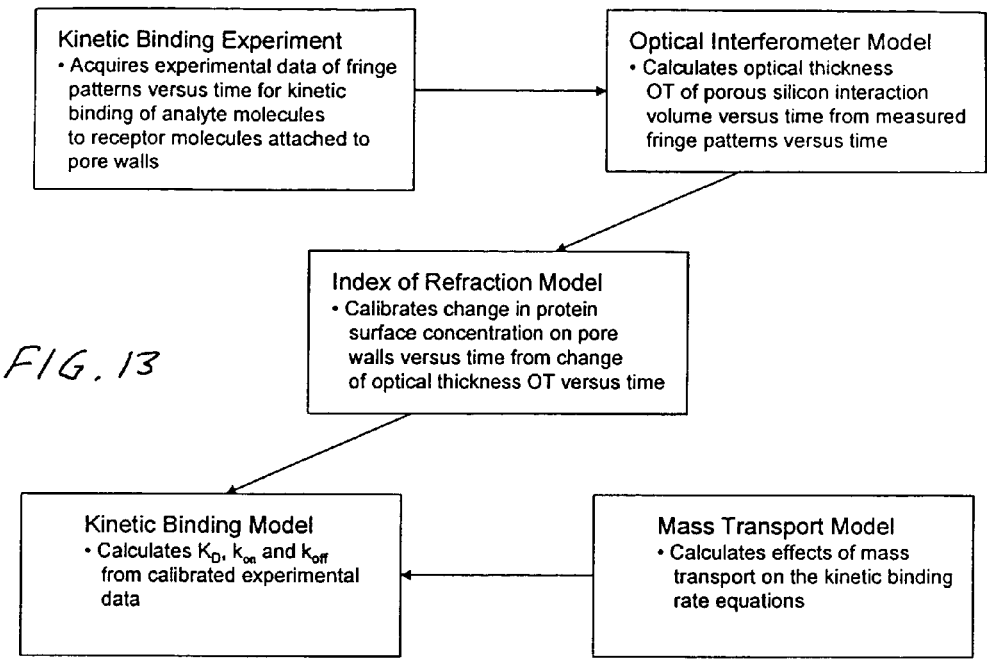
FIG. 13 shows the major steps of a computer program for calculating binding parameters.

The basic kinetic binding model, displayed in FIG. 10, assumes that a finite collection of ligand molecules 122, at concentration $[B]_o$ (units pg/mm$^2$), are immobilized, or spatially fixed, on the wall of pores 90 of the porous silicon interaction volume 202. This model assumes as shown in FIGS. 10 and 11 that at time t=0, a concentration $[A]_o$ (units [M] or mol/L) of analyte molecules 124 in buffer solution, are flowed at velocity v through flow channel 61 and are transported into interaction volume 202 by the diffusion process. The total number of analyte molecules 124, and the velocity v, are both large enough so that the concentration $[A]_o$ of unbound analyte molecules 124 remains constant in interaction volume 202 during the binding measurement time. The analyte molecules 124 bind, or associate, with the ligand molecules 122, at a characteristic rate $[A]k_{on}$ (units sec$^{-1}$), to form bound, immobilized molecules AB 127. The bound molecules AB 127 also unbind, or disassociate, at characteristic rate $k_{off}$ (units sec$^{-1}$) into the mobile analyte molecules 124 and the immobilized receptor molecules 122. At the time t=$t_{stop}$, the concentration of analyte molecules 124 is abruptly reduced to zero by the researcher so that only buffer solution is flowing through flow channel 61. The bound molecules AB 127 dissociate at characteristic rate $k_{off}$ (units sec$^{-1}$), and the resulting unbound analyte molecules 124 diffuse out of interaction volume 202 into flow channel 61, and are flowed to the waste outlet port 48, 50, or 54.

The differential rate equations that describe the binding and unbinding process are given by:

$$\frac{d[AB]}{dt} = k_{on}[A][B] - k_{off}[AB]$$

$$[B] = [B]_o - [AB]$$

$$\frac{d[B]_o}{dt} = 0$$

Eqs. (49)

with boundary conditions $[A](t)=0$ and $[AB](t)=0$ for $t<0$ (the initiation time period)

$[A](t)=[A]_o$ for $0<t<t_{stop}$ (the association time period)    Eqs. (50)

$[A](t)=0$ for $t>t_o$ (the dissociation time period).

The boundary conditions for the analyte molecules A given by equations 41 are displayed in FIG. 11.

An important constraint to note is that the concentration of available receptor molecules 122 $[B](t)$ is initially set by the experimenter at $[B](t)=[B]_o$ at time t=0, but decreases as the concentration of bound molecules $[AB](t)$ increases. The concentration of available analyte molecules 124 is controlled to be constant at $[A](t)=[A]_o$ during the association time period $0<t<t_o$ 130 due to the continual flow of new analyte molecules 124 to the interaction volume. Also, the concentration of available analyte molecules 124 is controlled by the researcher to be constant at $[A](t)=0$ for the initiation time period $t<0$ 128, and the dissociation time period $t>t_{stop}$ 132 due to a continual flow of buffer solution (i.e. zero concentration of analyte molecules 126) during this time periods.

The set of equations (49) are combined as $$\frac{d[AB](t)}{dt} = k_{on}[A](t)\{[B]_o - [AB](t)\} - k_{off}[AB](t) \quad \text{Eq. (51)}$$

Figure 12:
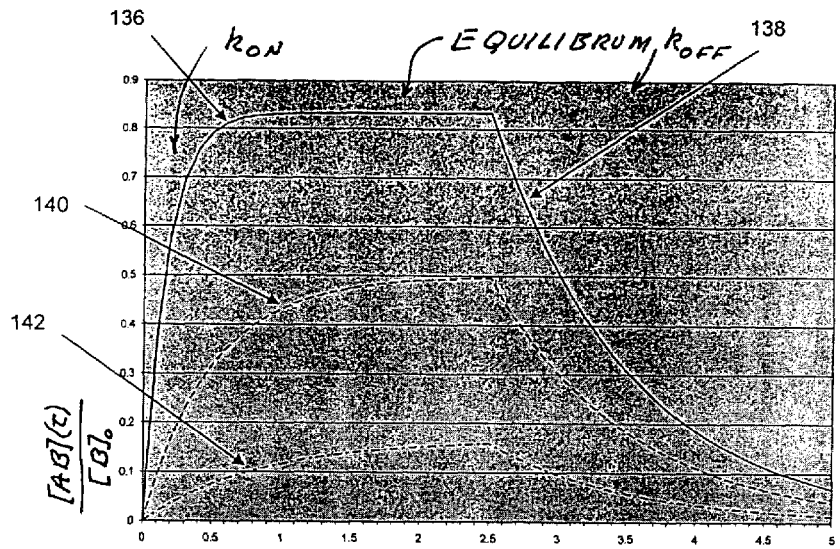
FIG. 12 shows graphs representing bound molecules as a function of time for the FIG. 11 situation.

Equation 51 is solved as $$[AB](t) = 0 \quad t<0 \quad \text{Eq. (52)}$$

$$[AB](t) = \frac{[B]_o\{1 - \exp(-(1+[A]_o/K_D)k_{off}t)\}}{1+\frac{K_D}{[A]_o}} \quad 0<t<t_o$$

$$[AB](t) = \frac{[AB](t_o)\exp(-k_{off}t)}{1+\frac{K_D}{[A]_o}} \quad t>t_o$$

where $K_D=k_{off}/k_{on}$ (units [M]). $(K_D)^{-1}$ is called the affinity and is indicative of the strength of interaction between analyte molecules A and ligand molecules B. FIG. 12 displays equations 52 $[AB](t)/[B]_o$ versus time t for three different concentrations $[A]_o$; $[A]_o=5K_D$, $[A]_o=K_D$, and $[A]_o=K_D/5$. There are several important features of equation 52. The concentration $[AB](t)$ of bound molecules AB reaches equilibrium $$[AB]_{eq} = \frac{[B]_o}{1+\frac{K_D}{[A]_o}} \quad \text{Eq. (53)}$$

during the association time period in a time scale $$\tau_{assoc} \approx \left[\frac{[A]_o}{K_D}k_{off}\right]^{-1},$$

and decreases to zero during the dissociation time period in a time scale $\tau_{dissoc}=k_{off}^{-1}$ during the dissociation time period. The parameter $K_D$ sets the scale of the equilibrium concentration $[AB]_{eq}$ of the bound molecules AB. If the experimenter sets the concentration of analyte molecules $[A]_o=K_D$, then the equilibrium concentration $[AB]_{eq}=[B]_o/2$ where $[B]_o$, the concentration of the receptor molecules B, is a parameter that the experimenter also initially sets. For higher concentrations $[A]_o\approx 10\,K_D$, the equilibrium concentration of bound molecules AB saturates to $[AB]_{eq}=[B]_o$. For lower concentrations $[A]_o<0.5\,K_D$, the equilibrium concentration decreases as $[AB]_{eq}\approx([A]_o/K_D)[B]_o$.

Example of a Kinetic Binding Measurement

This section demonstrates a typical kinetic binding experiment of a typical protein-protein interaction. The ligand molecule 122 is a monoclonal antibody-Anti TSH (thyroid stimulating hormone), with a 150 kDa molar mass and two binding sites per ligand molecule 122. The analyte molecule 124 is a TSH protein, with a 28 kDa molar mass. The experimentally derived kinetic binding data for this interaction are $k_{on}=2\times10^5$ ($M^{-1}$ $s^{-1}$), $k_{off}=2\times10^{-3}$($s^{-1}$), and $K_D=10$ nM. These proteins can be used to perform tests on the FIG. 1 device to confirm that the FIG. 1 device produces results consistent with the known binding rates.

A typical binding experiment attempts to determine the values of $k_{on}$, $k_{off}$, and $K_D$, by measuring the binding data of the type displayed in FIG. 12 for one ligand concentration $[B]_o$ and the several (e.g. three to ten) different analyte concentration $[A]_o$ such as three different concentrations (136, 140 and 142) as shown in FIG. 12. The approximate range that $[A]_o$ is varied is typically from $[A]_o=0.1$ $K_D$ to $[A]_o=10$ $K_D$. The concentrations $[A]_o$, as well as the actual timescale $t$ of the binding experiments, should be measured with care because these values are used in the analysis of the binding curve data to calculate the final values of $k_{on}$, $k_{off}$, and $K_D$. The actual values of the ligand concentrations $[B]_o$ do not need to be measured because these values are not used in the final calculation of $k_{on}$, $k_{off}$, and $K_D$; however, the analysis assumes that the value of $[B]_o$ is held constant over the entire series of binding experiments. The preferred device shown in FIG. 1 can perform four measurements simultaneously.

Figure 14:
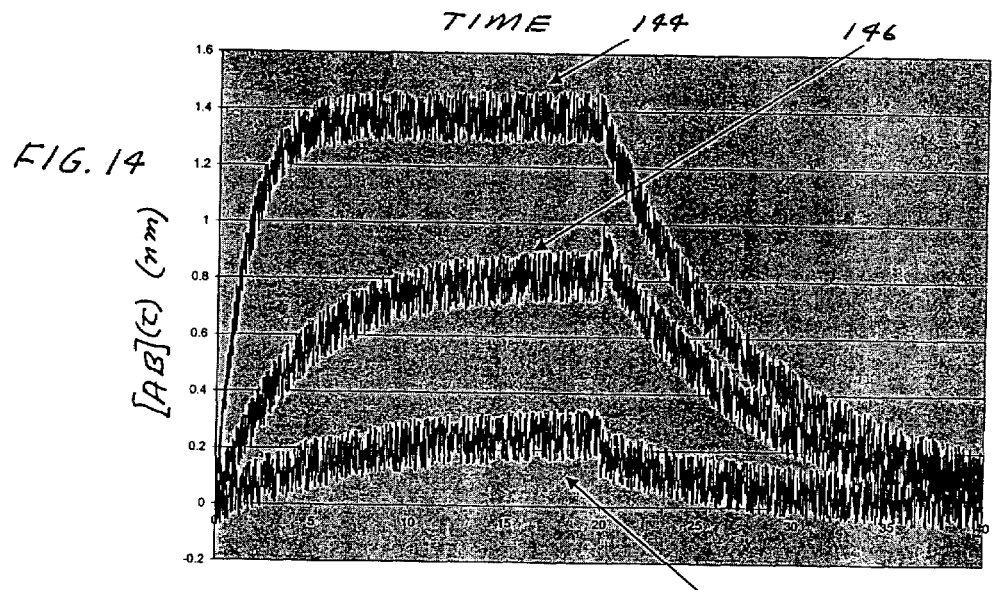
FIG. 14 is the same as FIG. 12 with noise simulated.

FIGS. 12 and 14 displays simulated results of a kinetic binding experiment for anti-TSH/TSH system based on Equation 52. They are the same except that FIG. 14 includes simulated noise. The parameters of the porous silicon interaction volume are L=2000 nm, d=120 nm, P=0.80. The simulated device noise is 1 part per million of the measured optical thickness. The surface concentration of the TSH-antibody was set at F=0.1. Equation (4) shows that the initial OPD for this experiment is approximately OPD=2(2000 nm)(1.804)=7216 nanometers, or nm. Preparation of the pores with ligand molecules (F=0.1) results in a change in OPD by ΔOPD=2(2000 nm)(0.0115)(0.1)=4.6 nm. Ligands are immobilized in the pores 90 using the feature of the FIG. 1 device which permits an operator to monitor the immobilization process in interaction region 202 so the experimenter can stop the ligand molecule 122 coverage when the OPD increases from OPD=7216 nm to OPD=7216 nm+4.6 nm=7220.6 nm. The TSH molecules are introduced to the interaction volume 202 at three different concentrations, $[A]_0=25$ nM, $[A]_o=5$ nM, and $[A]_o=1$ nM (144, 146 and 148, respectively). For each experiment, after a 5 minute binding, or association, time period, the concentration of TSH molecules is switched to $[A]_0=0$, and the dissociation time period is measured for another 5 minutes.

If we measure the concentration of receptor molecules $[B]_o$ and the concentration of bound molecules $[AB](t)$ in OPD units (nm), then the maximum, or saturation, value of the bound molecules, $$[AB]_{max} = \left(\frac{2M_A}{M_B}\right)[B]_o \qquad \text{Eq. (54)}$$

where $M_A=28$ kDa, $M_B$ KDa, and the factor of 2 accounts for two binding sites per analyte molecule for this particular interaction. This gives $[AB]_{max}=1.7$ nm.

Alternate Embodiments

FIG. 15B shows an alternate embodiment of the porous silicon interferometer that utilizes the interferometer path $\overline{AD}$ as the signal path and the interferometer path $\overline{AB+BC}$ as the reference path. This embodiment incorporates a substantial amount of the operational features discussed above. However, the path length $\overline{AD}$ 30 is given by $$\overline{AD} = \frac{2Ln_r(buffer)\sin^2\theta_i}{n_r(ps)\sqrt{1-\left(\frac{n_r(buffer)}{n_r(ps)}\sin^2\theta_i\right)}}. \qquad \text{Eq. (56)}$$

For $\theta_i=10$ degrees, equation (56) gives $\overline{AD}=0.0499L$; thus a porous silicon depth L=4000 nm gives $\overline{AD}=180$ nm. For this embodiment, protein receptor molecules immobilized in the top interaction volume 150 interact with analyte molecules flowing through flow channel 61 and diffusing into top interaction volume 150. The optical path difference defined by equation (4) changes due to binding interactions of analyte molecules with receptor molecules and the optical path difference changes are measured in the same manner as described for the preferred embodiment. The major difference between this embodiment and the preferred embodiment the optical path length corresponding to path $\overline{AB+BC}$ remains constant, thus acting as the reference path of the optical interferometer. The reference path is realized by fabricating the porous silicon volume 152 so that the index of refraction $n_r(ps)$ remains constant. The preferred method for the fabrication of the porous silicon reference volume 152 involve the etching of very small pore diameters 90, on the order of 5 nm, so that large protein molecules cannot diffuse into the pores 90. Another fabrication method involves the filling of the pores 90 with a polymer so that neither proteins nor buffer solution will enter the pores 90. Another fabrication method involves the use of a thin film non-porous volume 152 that acts as the reference path. This alternate embodiment enables the immobilization of receptor molecules in a cellular membrane that comprises the interaction volume 150. Measurement of analyte molecules interacting with the receptor molecules in the cellular membrane enables the study of protein interactions in a more natural environment.

Another embodiment of the porous silicon interferometer involves highly sensitive measurements of gaseous chemical species, such as G-type nerve agents or volatile organic chemicals (VOCs), for example. The modifications from the preferred embodiment primarily involve modifications of the pore etching parameters, modifications of the chemical preparation of the pores 90, and the modification to a gaseous delivery subsystem. For example, typical gaseous chemical molecules are much smaller than large protein molecules, so the diameters and depths of pores 90, for this embodiment, are in the 5-15 nm and 10-50 micron range, respectively. As an example of alternate chemical preparation steps, the G-type nerve agents feature a phosphate ($R-PO_4^{2-}$) molecular backbone complex and a phosphorous fluorine (P—F) molecular complex. The P—F bond can be cleaved with the use of a copper catalyst with hydrofluoric acid released as a by-product. The hydrofluoric acid further etches the porous structure, thereby resulting in a measurable change in the OPD.

While the present invention is described in terms of preferred embodiments, the reader should understand that these are merely examples and that many other embodiments are changes to the above embodiments will be obvious to persons skilled in this art. For example, the size, shape and number of pores in the porous silicon regions could vary greatly depending on the particular application of the present invention. In most cases the number of pores in each region will be far more than 1000. The porosity of the regions may vary greatly with the application. In preferred embodiments Applicants have chosen porosity values of the porous silicon region to produce an index of refraction for the water-filled porous silicon region of n=1.8 as compared to an n=3.7 for silicon and n=1.3 for the water. However, in many cases many other porosity values could be utilized. Many and various chemistries can be utilized in the porous silicon reaction chambers other than the ones specifically disclosed. The porous silicon regions can utilized to act as alternate capture mechanisms. For example, rows of reaction chambers can be created with a different chemistry in each row. With such a setup, it is possible to create interaction zones with a first chemistry that permits separation of certain kinds of molecules from a larger "soup" of molecules. Then a capture mechanism can be used that more selectively binds with molecules of interest with higher resolution than would otherwise be measurable in the presence of a higher abundance of molecules. Also various optical detection methods can be used other than the ones specifically described. F or example, it is known that Ramon spectroscopy is of considerably value in determining molecular structure and chemical analysis. Therefore, Ramon spectroscopy techniques can be adapted for use with the porous silicon observation regions and micro fluidic sample control techniques of present invention. Quad cell detection is an additional optical detection technique that could be utilized to detect changes in molecular activity in the observation regions described in the specification. In addition, other optical observation techniques may be adaptable for use in connection with the present invention. In some cases it may be desirable to utilize mass spectrometry detection techniques along with the optical detection techniques described herein to more precisely define molecular components and their activity. Therefore, the scope of the invention should be determined by the claims and their legal equivalents.

We claim:

1. An optical sensor for monitoring molecular binding interactions, said sensor comprising:
   A) at least one porous silicon region comprising more than 1000 pores, each pore having a nominal width and a nominal depth at least 10 times larger than said nominal width, with the depth of each pore being approximately equal to the depth of at least most other pores in said porous silicon region, said porous silicon region defining a top surface and a bottom surface, and said bottom surface being parallel or approximately parallel to said top surface;
   B) at least one buffer-sample fluid flow channel located above said at least one porous silicon region providing a fluid flow passage across said porous silicon region;
   C) at least one light source for illuminating said at least one porous silicon region;
   D) at least one interference monitor adapted to monitor interference patterns caused by interference of light reflected from said top surface with light reflected from said bottom surface of said at least one porous silicon region, said interference monitor comprising a deep well linear photodiode array of pixels, each pixel having a photoelectron full well capacity of about 156 million photoelectrons or more, and having a frame rate of about one hundred or more frames of interference fringe data per second;
   E) a fluid flow control system for producing controlled flow of buffer solutions, ligand containing solutions, and analyte containing solutions through said at least one fluid flow channel; and
   F) a computer processor programmed with a computer program causing said processor to execute molecular binding measurements based on changes in the interference patterns monitored by the at least one interference monitor while analytes bind with and disassociate from ligands attached to surfaces of said pores, said computer program comprising executable instructions for calculating optical path differences in measured interference fringe patterns that are correlated to a test fringe pattern, wherein the test fringe pattern varies sinusoidally as a function of optical path differences divided by the wavelength of said light.

2. The optical sensor as in claim 1 wherein said at least one porous silicon region is a plurality of porous silicon regions, said at least one buffer-sample fluid flow channel is a plurality of fluid flow channels, said at least one light source is a plurality of light sources and said at least one spectral monitor is a plurality of spectral monitors.

3. The optical sensor as in claim 2 wherein said plurality of porous silicon regions is at least four porous silicon regions.

4. The optical sensor as in claim 1 wherein said molecular binding measurements are kinetic molecular binding measurements.

5. The optical sensor as in claim 1 wherein said at least one interference monitor is at least one spectrometer.

6. The optical sensor as in claim 1 wherein said at one interference monitor comprises at least one photo diode array.

7. The optical sensor as in claim 1 wherein said porous silicon region is located on a silicon substrate.

8. The optical sensor as in claim 7 wherein said silicon substrate is p+ +-type silicon with a <100> crystalline configuration.

9. The optical sensor as in claim 7 wherein said porous silicon region is incorporated into a fluidics cartridge comprising fluid flow channels and a plurality of flow control valves, said fluid flow channels being in flow communication with said at least one buffer-sample fluid flow channel.

10. The optical sensor as in claim 9 wherein said valves are pneumatically operated pinch valves.

11. The optical sensor as in claim 10 wherein said pinch valves are computer controlled.

12. The optical sensor as in claim 1 wherein said nominal widths of said pores are within the range of about 80 to 120 nanometers and said nominal depths of said pores are within a range of about 1000 to 3000 nanometers.

13. The optical sensor as in claim 9 and also comprising a fluidics enclosure in which said fluidics cartridge is removably installed.

14. The optical sensor as in claim 13 and also comprising robotic equipment for injecting ligand containing samples and analyte-containing samples into said fluidics enclosure.

15. The optical sensor as in claim 1 and also comprising sample trays, at least one buffer fluid tank, at least one waste tank, a sample pump, a buffer pump and pneumatic controls, firmware and software for automated real-time measurement of kinetic binding reactions.

16. The optical sensor as in claim 14 and also comprising sample trays, at least one buffer fluid tank, at least one waste tank, a sample pump, a buffer pump and pneumatic controls, firmware and software for automated real-time measurement of kinetic binding reactions.

17. The optical sensor as in claim 1 wherein said at least one light source comprises a white light source or an approximately white light source.

18. The optical sensor as in claim 1 wherein said at least one light source comprises a narrowband light source.

19. The optical sensor as in claim 1 wherein said at least one light source comprises and ultraviolet light source.

20. The optical sensor as in claim 1 wherein said at least one light source comprises an infrared light source.

21. The optical sensor as in claim 1 wherein said pores comprise carboxylic acid functionalized surfaces.

22. The optical sensor as in claim 21 and also comprised linker molecules attached to said carboxylic acid functionalized surfaces.

23. The optical sensor as in claim 22 wherein said linker molecules comprise PEG molecules.

24. The sensor as in claim 23 wherein most of said PEG molecules comprise four monomers.

25. The sensor as in claim 23 wherein most of said PEG molecules have a total length of about 19.2 Angstroms.

26. The optical sensor as in claim 1 wherein said computer program comprises algorithms for calculating changes in apparent optical path differences based on said changes in said spectral interference patterns.

27. The optical sensor as in claim 1 wherein said at least one interference monitor comprises a quad cell.

28. The optical sensor as in claim 1 wherein said nominal width of said pores in said porous silicon region is chosen to produce a modulation index for optimizing optical resolution.

29. The optical sensor as in claim 1 wherein said nominal width of said pores in said porous silicon region is chosen to produce a modulation index for optimizing kinetic binding assays.

30. A method for measuring molecular binding interactions, utilizing an optical sensor comprising:
   a) at least one porous silicon region comprising more than 1000 pores, each pore having a nominal width and a nominal depth at least 10 times larger than said nominal width, with the depth of each pore being approximately equal to the depth of at least most other pores in said porous silicon region, said porous silicon region defining a top surface and a bottom surface, and said bottom surface being parallel or approximately parallel to said top surface;
   b) at least one buffer-sample fluid flow channel located above said at least one porous silicon region providing a fluid flow passage across said porous silicon region;
   c) at least one light source for illuminating said at least one porous silicon region;
   d) at least one interference monitor adapted to monitor interference fringe patterns caused by interference of light reflected from said top surface with light reflected from said bottom surface of said at least one porous silicon region, said interference monitor comprising a deep well linear photodiode array of pixels, each pixel having a photoelectron full well capacity of about 156 million photoelectrons or more, and having a frame rate of about one hundred or more frames of interference fringe data per second;
   e) a fluid flow control system for producing controlled flow of buffer solutions, ligand containing solutions, and analyte containing solutions through said at least one fluid flow channel; and
   f) a computer processor programmed with a computer program causing said processor to execute kinetic binding measurements based on changes in the spectral interference patterns monitored by the at least one interference monitor while analytes bind with and disassociate from ligands attached to surfaces of said pores, said computer program comprising executable instructions for calculating optical path differences in measured interference fringe patterns that are correlated the measured interference fringe patterns to a test fringe pattern, wherein the test fringe pattern varies sinusoidally as a function of optical path differences divided by the wavelength of said light, wherein said method comprises:
   A) immobilizing ligand molecules within said pores;
   B) causing a solution containing analyte molecules to flow across said porous silicon region to permit analyte molecules to diffuse close to and become bound at least temporarily to said ligand molecules to form interference fringe patterns;
   C) illuminating at least a portion of said porous silicon region so as to produce reflections from said bottom surface and said top surface; and
   D) monitoring changes in interference fringe patterns produced by light reflected from said top and bottom surfaces in order to obtain information concerning binding reactions between said ligand and said analyte.

31. The method as in claim 30 and further comprising a step following Step B of causing a buffer solution to flow across said porous silicon region wherein analytes that have become bound to ligands during step B become disassociated from said ligands.

32. The method as in claim 31 and further comprising the step of monitoring changes in spectral patterns produced by light reflected from said top and bottom surfaces in order to obtain information concerning disassociation reactions between said ligand and said analyte.

33. The method as in claim 31 and further comprising the steps of: A) acquiring a reference pattern; B) acquiring a spectral interference pattern; C) normalizing said reference pattern and said spectral interference pattern; D) calculating a first derivative of a corresation function using said normalilzed spectral interference pattern and said normalized reference pattern; E) calculating a zero crossing of said first derivative of said correlation function; and F) recording said zero crossing as an optical path difference.

34. The method as of claim 30 wherein a region above and adjacent to said at least one porous silicon region provides a reference optical path length for producing interference effects.

35. The method as of claim 30 wherein said porous silicon region provides a reference optical path length for producing interference effects.

36. An optical sensor for monitoring molecular binding interactions, said sensor comprising:
   A) at least one porous silicon region comprising more than 1000 pores, each pore having a nominal width and a nominal depth at least 10 times larger than said nominal width, with the depth of each pore being approximately equal to the depth of at least most other pores in said porous silicon region, said porous silicon region defining a top surface and a bottom surface, and said bottom surface being parallel or approximately parallel to said top surface;
   B) at least one buffer-sample fluid flow channel located above said at least one porous silicon region providing a fluid flow passage across said porous silicon region;
   C) at least one light source for illuminating said at least one porous silicon region;
   D) at least one interference monitor adapted to monitor interference patterns caused by interference of light reflected from said top surface with light reflected from said bottom surface of said at least one porous silicon region, said interference monitor comprising a deep well linear photodiode array of pixels, each pixel having a photoelectron full well capacity of about 156 million photoelectrons or more, and having a frame rate of about one hundred or more frames of interference fringe data per second;

E) a fluid flow control system for producing controlled flow of buffer solutions, ligand containing solutions, and analyte containing solutions through said at least one fluid flow channel; and F) a processor means programmed with a computer program causing said processor means to execute kinetic molecular binding measurements based on changes in the interference patterns monitored by the at least one interference monitor while analytes bind with and disassociate from ligands attached to surfaces of said pores, said computer program comprising executable instructions for calculating optical path differences in measured interference fringe patterns that are correlated to a test fringe pattern, wherein the test fringe pattern varies sinusoidally as a function of optical path differences divided by the wavelength of said light.

37. The sensor as in claim 33 wherein said processor means includes a graph forming means for producing a graph of OPD vs time during periods of ligand-analyte association and ligand-analyte disassociation.

38. The sensor as in claim 33 wherein said processor means includes a computer program for determining values of rate constants $k_{on}$ and $k_{off}$.

39. An optical sensor for monitoring molecular binding interactions, said sensor comprising:

A) at least one porous silicon region, said porous silicon region defining a top surface and a bottom surface, and said bottom surface being parallel or approximately parallel to said top surface;

B) at least one buffer-sample fluid flow channel located above said at least one porous silicon region providing a fluid flow passage across said porous silicon region;

C) at least one light source for illuminating said at least one porous silicon region;

D) at least one interference monitor adapted to monitor interference patterns caused by interference of light reflected from said top surface with light reflected from said bottom surface of said at least one porous silicon region, said interference monitor comprising a deep well linear photodiode array of pixels, each pixel having a photoelectron full well capacity of about 156 million photoelectrons or more, and having a frame rate of about one hundred or more frames of interference fringe data per second;

E) a fluid flow control system for producing controlled flow of buffer solutions, ligand containing solutions, and analyte containing solutions through said at least one fluid flow channel; and F) a computer processor programmed with a computer program causing said processor to execute molecular binding measurements based on changes in the interference patterns monitored by the at least one interference monitor while analytes bind with and disassociate from ligands attached to surfaces of said pores, said computer program comprising executable instructions for calculating optical path differences in measured interference fringe patterns that are correlated to a test fringe pattern, wherein the test fringe pattern varies sinusoidally as a function of optical path differences divided by the wavelength of said light.

40. An optical sensor for monitoring molecular binding interactions, said sensor comprising:

A) at least one porous silicon region comprising more than 1,000 pores, each pore having a nominal width and a nominal depth at least 10 times larger than said nominal width, with the depth of each pore being approximately equal to the depth of at least most other pores in said porous silicon region, said porous silicon region defining a top surface and a bottom surface, and said bottom surface being parallel or approximately parallel to said top surface;

B) at least one buffer-sample fluid flow channel located above said at least one porous silicon region providing a fluid flow passage across said porous silicon region;

C) at least one light source for illuminating said at least one porous silicon region;

D) at least one interference monitor adapted to monitor interference patterns caused by interference of light reflected from said top surface with light reflected from said bottom surface of said at least one porous silicon region, said interference monitor comprising a deep well linear photodiode array of pixels, each pixel having a photoelectron full well capacity of about 156 million photoelectrons or more, and having a frame rate of about one hundred or more frames of interference fringe data per second;

E) a fluid flow control system for producing controlled flow of buffer solutions, ligand containing solutions, and analyte containing solutions through said at least one fluid flow channel; and F) a computer processor programmed with a computer program causing said processor to execute molecular concentration measurements based on changes in the interference patterns monitored by the at least one interference monitor while analytes bind with and disassociate from ligands attached to surfaces of said pores, said computer program comprising executable instructions for calculating optical path differences in measured interference fringe patterns that are correlated to a test fringe pattern, wherein the test fringe pattern varies sinusoidally as a function of optical path differences divided by the wavelength of said light.

41. The optical sensor as in claim 1 wherein said at least one porous silicon region is a plurality of porous silicon regions with more than one of said plurality of porous silicon regions having ligands immobilized within them that are different from ligands immobilized in other porous silicon regions.

42. The optical sensor as in claim 1 and further comprising a mass spectrometer.

43. The optical sensor as in claim 1 wherein said is adapted to produce fringe patterns with signal to noise ratios of about 90,000.

44. The optical sensor as in claim 1 wherein the test fringe pattern is described by:

$$I_x(X;\lambda) = I_{10}(\lambda)[1 - M\cos(2\pi X/\lambda)]$$

45. The optical sensor as in claim 44 where X is a varying test optical thickness, using a correlation integral defined by:

$$C(X) = \frac{1}{M}\int_{-\infty}^{\infty} d\lambda [I_T(X;\lambda) - I_{ro}(\lambda)][I_r(\lambda) - I_{ro}(\lambda)]$$

wherein optical path differences are calculated form the correlation integral as the value X corresponding to a peak of C(X) and the value of X is precisely determined by locating a zero crossing of a first derivative of C(X) with respect to X or C'(X).

* * * * *